US005665346A

United States Patent [19]
Clark-Lewis et al.

[11] Patent Number: 5,665,346
[45] Date of Patent: Sep. 9, 1997

[54] HUMAN INTERLEUKIN-8 ANALOGS

[75] Inventors: Ian Clark-Lewis, Vancouver, Canada; Bernhard Moser, Bern, Switzerland

[73] Assignee: Research Corporation Technologies, Inc., Tucson, Ariz.

[21] Appl. No.: 244,702

[22] PCT Filed: Dec. 3, 1992

[86] PCT No.: PCT/CA92/00528

§ 371 Date: Sep. 27, 1994

§ 102(e) Date: Sep. 27, 1994

[87] PCT Pub. No.: WO93/11159

PCT Pub. Date: Jun. 10, 1993

Related U.S. Application Data

[63] Continuation-in-part of Ser. No. 801,578, Dec. 4, 1991, abandoned.

[51] Int. Cl.$^6$ .......................... A61K 38/20; A61K 38/19; C07K 14/52; C07K 14/54
[52] U.S. Cl. .......................... 424/85.2; 514/12; 530/324; 530/351; 530/402; 930/141
[58] Field of Search ...................... 530/351, 324, 530/402; 514/12; 424/85.2; 930/141

[56] References Cited

U.S. PATENT DOCUMENTS

| 5,079,228 | 1/1992 | Cohen et al. | 514/12 |
|---|---|---|---|
| 5,093,242 | 3/1992 | Bachmair et al. | 435/69.7 |
| 5,290,550 | 3/1994 | Fisher et al. | 424/85.2 |
| 5,302,384 | 4/1994 | Gimbrone, Jr. et al. | 424/85.2 |

FOREIGN PATENT DOCUMENTS

| 8904836 | 6/1989 | WIPO. |
| 9108231 | 6/1991 | WIPO. |
| 9108483 | 6/1991 | WIPO. |
| 9204372 | 3/1992 | WIPO. |

OTHER PUBLICATIONS

Clore, G. Marius, et al; (1990) *Biochem.*, 29, pp. 1689–1696.
Clore, G. Marius, et al; (1989) *The Journal of Biological Chemistry*, 264, pp. 18907–18911.
Sticherling, Michael, et al; (1989) *J. Immunol.*, 143, pp. 1628–1634.
Leonard, Edward J., et al; (1991) *Journal of Leukocyte Biology*, 49, pp. 258–265.
Clark-Lewis, Ian, et al; (1991) *Journal of Biological Chemistry*, 266, pp. 23128–23134.
Hebert, C.A., et al; (1991) *Journal of Biological Chemistry*, 266, pp. 18989–18994.
Matsushima, K. and Oppenheim, J.J.; (1989) *Cytokine*, 1:2–13, at pp. 7–8 and Fig.6.
Yoshimura, T., et al; (1989) *Mol. Immunol.*, 26:87–93, at p. 91 (Fig.4).
Gregory, H., et al; (1988) *Biochem. Biophys. Res. Commun.*, 151:883–890 at p. 886 (Fig.1).
Matsushima, K., et al; (1988) *J. Exp. Med.*, 167:1883–1893, at p. 1886 (Fig.1).
Walz, A. and Baggiolini, M.; (1989) *Biochem. Biophys. Res. Commun.*, 159:969–975, at p. 973 (Fig.4).
Richmond, A., et al; (1988) *The EMBO Journal*, 7:2025–2033, at pp. 2026–2027 (Fig.2&3).
Clark-Lewis, I., et al; (1991) *Biochemistry*, 30:3128–3135.
Lindley, I., et al; (1988) *Proc. Natl. Acad. Sci. USA*, 85:9199–9203, at pp. 9200–9201 (Fig.1 & 2).

*Primary Examiner*—Mindy Fleisher
*Assistant Examiner*—Nancy J. Degen
*Attorney, Agent, or Firm*—Scully, Scott, Murphy & Presser

[57] ABSTRACT

The present invention provides human interleukin-8 (IL-8) analogs that are modified in the Glu4 Leu5 Arg6 region, and have a core structure corresponding to the IL-8 (7–51) sequence are provided. These neutrophil binding analogs display altered IL-8 activities that can be exploited for therapeutic and other purposes. Such antagonists include those in which, for example, the Leu5 and/or Arg6 residues are replaced, and in which the Glu4 and/or Leu5 residues are deleted. Also provided are biologically active human interleukin-8 (IL-8) analogs comprising a core sequence that includes IL-8 (1–51), IL-8 (3–51) or IL-8 (4–51). The invention also provides pharmaceutical compositions containing the aforementioned analogs.

28 Claims, 13 Drawing Sheets

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 72 amino acids
        ( B ) TYPE: amino acid
        ( D ) TOPOLOGY: linear ( x i ) SEQUENCE DESCRIPTION: SEQ ID NO:1:

```
Ser Ala Lys Glu Leu Arg Cys Gln Cys Ile Lys Thr Tyr Ser Lys Pro
 1               5                  10                  15

Phe His Pro Lys Phe Ile Lys Glu Leu Arg Val Ile Glu Ser Gly Pro
                20                  25                  30

His Cys Ala Asn Thr Glu Ile Ile Val Lys Leu Ser Asp Gly Arg Glu
            35                  40                  45

Leu Cys Leu Asp Pro Lys Glu Asn Trp Val Gln Arg Val Val Glu Lys
        50                  55                  60

Phe Leu Lys Arg Ala Glu Asn Ser
65                  70
```

( 2 ) INFORMATION FOR SEQ ID NO:2:

( i ) SEQUENCE CHARACTERISTICS:
        ( A ) LENGTH: 69 amino acids
        ( B ) TYPE: amino acid
        ( D ) TOPOLOGY: linear ( x i ) SEQUENCE DESCRIPTION: SEQ ID NO:2:

```
Glu Leu Arg Cys Gln Cys Ile Lys Thr Tyr Ser Lys Pro Phe His Pro
 1               5                  10                  15

Lys Phe Ile Lys Glu Leu Arg Val Ile Glu Ser Gly Pro His Cys Ala
                20                  25                  30

Asn Thr Glu Ile Ile Val Lys Leu Ser Asp Gly Arg Glu Leu Cys Leu
            35                  40                  45
```

```
Asp Pro Lys Glu Asn Trp Val Gln Arg Val Val Glu Lys Phe Leu Lys
    50                      55                  60

Arg Ala Glu Asn Ser
65
```

(2) INFORMATION FOR SEQ ID NO:3:

(i) SEQUENCE CHARACTERISTICS:
       (A) LENGTH: 69 amino acids
       (B) TYPE: amino acid
       (D) TOPOLOGY: linear (xi) SEQUENCE DESCRIPTION: SEQ ID NO:3:

```
Glu Leu Gln Cys Gln Cys Ile Lys Thr Tyr Ser Lys Pro Phe His Pro
1               5                   10                  15

Lys Phe Ile Lys Glu Leu Arg Val Ile Glu Ser Gly Pro His Cys Ala
            20                  25                  30

Asn Thr Glu Ile Ile Val Lys Leu Ser Asp Gly Arg Glu Leu Cys Leu
        35                  40                  45

Asp Pro Lys Glu Asn Trp Val Gln Arg Val Val Glu Lys Phe Leu Lys
    50                      55                  60

Arg Ala Glu Asn Ser
65
```

(2) INFORMATION FOR SEQ ID NO:4:

(i) SEQUENCE CHARACTERISTICS:
       (A) LENGTH: 69 amino acids
       (B) TYPE: amino acid
       (D) TOPOLOGY: linear (xi) SEQUENCE DESCRIPTION: SEQ ID NO:4:

```
Glu Leu Leu Cys Gln Cys Ile Lys Thr Tyr Ser Lys Pro Phe His Pro
1               5                   10                  15

Lys Phe Ile Lys Glu Leu Arg Val Ile Glu Ser Gly Pro His Cys Ala
            20                  25                  30

Asn Thr Glu Ile Ile Val Lys Leu Ser Asp Gly Arg Glu Leu Cys Leu
        35                  40                  45

Asp Pro Lys Glu Asn Trp Val Gln Arg Val Val Glu Lys Phe Leu Lys
    50                      55                  60

Arg Ala Glu Asn Ser
65
```

(2) INFORMATION FOR SEQ ID NO:5:

(i) SEQUENCE CHARACTERISTICS:
       (A) LENGTH: 69 amino acids
       (B) TYPE: amino acid
       (D) TOPOLOGY: linear (xi) SEQUENCE DESCRIPTION: SEQ ID NO:5:

```
Glu Leu Lys Cys Gln Cys Ile Lys Thr Tyr Ser Lys Pro Phe His Pro
1               5                   10                  15

Lys Phe Ile Lys Glu Leu Arg Val Ile Glu Ser Gly Pro His Cys Ala
            20                  25                  30

Asn Thr Glu Ile Ile Val Lys Leu Ser Asp Gly Arg Glu Leu Cys Leu
        35                  40                  45

Asp Pro Lys Glu Asn Trp Val Gln Arg Val Val Glu Lys Phe Leu Lys
    50                      55                  60

Arg Ala Glu Asn Ser
65
```

(2) INFORMATION FOR SEQ ID NO:6:

(i) SEQUENCE CHARACTERISTICS:
 (A) LENGTH: 69 amino acids
 (B) TYPE: amino acid
 (D) TOPOLOGY: linear (ix) FEATURE:
 (A) NAME/KEY: Modified-site
 (B) LOCATION: 3
 (D) OTHER INFORMATION: /note= "Xaa = Orn"

(xi) SEQUENCE DESCRIPTION: SEQ ID NO:6:

| Glu | Leu | Xaa | Cys | Gln | Cys | Ile | Lys | Thr | Tyr | Ser | Lys | Pro | Phe | His | Pro |
|---|---|---|---|---|---|---|---|---|---|---|---|---|---|---|---|
| 1 | | | 5 | | | | | | 10 | | | | | 15 | |
| Lys | Phe | Ile | Lys | Glu | Leu | Arg | Val | Ile | Glu | Ser | Gly | Pro | His | Cys | Ala |
| | | | 20 | | | | | 25 | | | | | 30 | | |
| Asn | Thr | Glu | Ile | Ile | Val | Lys | Leu | Ser | Asp | Gly | Arg | Glu | Leu | Cys | Leu |
| | | 35 | | | | | 40 | | | | | 45 | | | |
| Asp | Pro | Lys | Glu | Asn | Trp | Val | Gln | Arg | Val | Val | Glu | Lys | Phe | Leu | Lys |
| | 50 | | | | | 55 | | | | | 60 | | | | |
| Arg | Ala | Glu | Asn | Ser | | | | | | | | | | | |
| 65 | | | | | | | | | | | | | | | |

(2) INFORMATION FOR SEQ ID NO:7:

(i) SEQUENCE CHARACTERISTICS:
 (A) LENGTH: 69 amino acids
 (B) TYPE: amino acid
 (D) TOPOLOGY: linear (ix) FEATURE:
 (A) NAME/KEY: Modified-site
 (B) LOCATION: 3
 (D) OTHER INFORMATION: /note= "Xaa = Nle"

(xi) SEQUENCE DESCRIPTION: SEQ ID NO:7:

| Glu | Leu | Xaa | Cys | Gln | Cys | Ile | Lys | Thr | Tyr | Ser | Lys | Pro | Phe | His | Pro |
|---|---|---|---|---|---|---|---|---|---|---|---|---|---|---|---|
| 1 | | | 5 | | | | | | 10 | | | | | 15 | |
| Lys | Phe | Ile | Lys | Glu | Leu | Arg | Val | Ile | Glu | Ser | Gly | Pro | His | Cys | Ala |
| | | | 20 | | | | | 25 | | | | | 30 | | |
| Asn | Thr | Glu | Ile | Ile | Val | Lys | Leu | Ser | Asp | Gly | Arg | Glu | Leu | Cys | Leu |
| | | 35 | | | | | 40 | | | | | 45 | | | |
| Asp | Pro | Lys | Glu | Asn | Trp | Val | Gln | Arg | Val | Val | Glu | Lys | Phe | Leu | Lys |
| | 50 | | | | | 55 | | | | | 60 | | | | |
| Arg | Ala | Glu | Asn | Ser | | | | | | | | | | | |
| 65 | | | | | | | | | | | | | | | |

(2) INFORMATION FOR SEQ ID NO:8:

(i) SEQUENCE CHARACTERISTICS:
 (A) LENGTH: 69 amino acids
 (B) TYPE: amino acid
 (D) TOPOLOGY: linear (xi) SEQUENCE DESCRIPTION: SEQ ID NO:8:

| Ala | Ala | Arg | Cys | Gln | Cys | Ile | Lys | Thr | Tyr | Ser | Lys | Pro | Phe | His | Pro |
|---|---|---|---|---|---|---|---|---|---|---|---|---|---|---|---|
| 1 | | | 5 | | | | | | 10 | | | | | 15 | |
| Lys | Phe | Ile | Lys | Glu | Leu | Arg | Val | Ile | Glu | Ser | Gly | Pro | His | Cys | Ala |
| | | | 20 | | | | | 25 | | | | | 30 | | |
| Asn | Thr | Glu | Ile | Ile | Val | Lys | Leu | Ser | Asp | Gly | Arg | Glu | Leu | Cys | Leu |
| | | 35 | | | | | 40 | | | | | 45 | | | |

```
            Asp  Pro  Lys  Glu  Asn  Trp  Val  Gln  Arg  Val  Val  Glu  Lys  Phe  Leu  Lys
                 50                      55                      60

Arg  Ala  Glu  Asn  Ser
                 65
```

( 2 ) INFORMATION FOR SEQ ID NO:9:

( i ) SEQUENCE CHARACTERISTICS:
        ( A ) LENGTH: 68 amino acids
        ( B ) TYPE: amino acid
        ( D ) TOPOLOGY: linear ( x i ) SEQUENCE DESCRIPTION: SEQ ID NO:9:

```
            Leu  Arg  Cys  Gln  Cys  Ile  Lys  Thr  Tyr  Ser  Lys  Pro  Phe  His  Pro  Lys
            1                   5                       10                      15

Phe  Ile  Lys  Glu  Leu  Arg  Val  Ile  Glu  Ser  Gly  Pro  His  Cys  Ala  Asn
                           20                      25                      30

Thr  Glu  Ile  Ile  Val  Lys  Leu  Ser  Asp  Gly  Arg  Glu  Leu  Cys  Leu  Asp
                           35                      40                      45

Pro  Lys  Glu  Asn  Trp  Val  Gln  Arg  Val  Val  Glu  Lys  Phe  Leu  Lys  Arg
                      50                      55                      60

Ala  Glu  Asn  Ser
                 65
```

( 2 ) INFORMATION FOR SEQ ID NO:10:

( i ) SEQUENCE CHARACTERISTICS:
        ( A ) LENGTH: 68 amino acids
        ( B ) TYPE: amino acid
        ( D ) TOPOLOGY: linear ( x i ) SEQUENCE DESCRIPTION: SEQ ID NO:10:

```
            Ile  Arg  Cys  Gln  Cys  Ile  Lys  Thr  Tyr  Ser  Lys  Pro  Phe  His  Pro  Lys
            1                   5                       10                      15

Phe  Ile  Lys  Glu  Leu  Arg  Val  Ile  Glu  Ser  Gly  Pro  His  Cys  Ala  Asn
                           20                      25                      30

Thr  Glu  Ile  Ile  Val  Lys  Leu  Ser  Asp  Gly  Arg  Glu  Leu  Cys  Leu  Asp
                           35                      40                      45

Pro  Lys  Glu  Asn  Trp  Val  Gln  Arg  Val  Val  Glu  Lys  Phe  Leu  Lys  Arg
                      50                      55                      60

Ala  Glu  Asn  Ser
                 65
```

( 2 ) INFORMATION FOR SEQ ID NO:11:

( i ) SEQUENCE CHARACTERISTICS:
        ( A ) LENGTH: 68 amino acids
        ( B ) TYPE: amino acid
        ( D ) TOPOLOGY: linear ( x i ) SEQUENCE DESCRIPTION: SEQ ID NO:11:

```
            Gln  Arg  Cys  Gln  Cys  Ile  Lys  Thr  Tyr  Ser  Lys  Pro  Phe  His  Pro  Lys
            1                   5                       10                      15

Phe  Ile  Lys  Glu  Leu  Arg  Val  Ile  Glu  Ser  Gly  Pro  His  Cys  Ala  Asn
                           20                      25                      30

Thr  Glu  Ile  Ile  Val  Lys  Leu  Ser  Asp  Gly  Arg  Glu  Leu  Cys  Leu  Asp
                           35                      40                      45

Pro  Lys  Glu  Asn  Trp  Val  Gln  Arg  Val  Val  Glu  Lys  Phe  Leu  Lys  Arg
                      50                      55                      60

Ala  Glu  Asn  Ser
                 65
```

( 2 ) INFORMATION FOR SEQ ID NO:12:

( i ) SEQUENCE CHARACTERISTICS:
        ( A ) LENGTH: 67 amino acids
        ( B ) TYPE: amino acid
        ( D ) TOPOLOGY: linear ( x i ) SEQUENCE DESCRIPTION: SEQ ID NO:12:

```
Arg Cys Gln Cys Ile Lys Thr Tyr Ser Lys Pro Phe His Pro Lys Phe
 1               5                  10                  15

Ile Lys Glu Leu Arg Val Ile Glu Ser Gly Pro His Cys Ala Asn Thr
            20                  25                  30

Glu Ile Ile Val Lys Leu Ser Asp Gly Arg Glu Leu Cys Leu Asp Pro
        35                  40                  45

Lys Glu Asn Trp Val Gln Arg Val Val Glu Lys Phe Leu Lys Arg Ala
    50                  55                  60

Glu Asn Ser
65
```

( 2 ) INFORMATION FOR SEQ ID NO:13:

( i ) SEQUENCE CHARACTERISTICS:
        ( A ) LENGTH: 66 amino acids
        ( B ) TYPE: amino acid
        ( D ) TOPOLOGY: linear ( x i ) SEQUENCE DESCRIPTION: SEQ ID NO:13:

```
Cys Gln Cys Ile Lys Thr Tyr Ser Lys Pro Phe His Pro Lys Phe Ile
 1               5                  10                  15

Lys Glu Leu Arg Val Ile Glu Ser Gly Pro His Cys Ala Asn Thr Glu
            20                  25                  30

Ile Ile Val Lys Leu Ser Asp Gly Arg Glu Leu Cys Leu Asp Pro Lys
        35                  40                  45

Glu Asn Trp Val Gln Arg Val Val Glu Lys Phe Leu Lys Arg Ala Glu
    50                  55                  60

Asn Ser
65
```

( 2 ) INFORMATION FOR SEQ ID NO:14:

( i ) SEQUENCE CHARACTERISTICS:
        ( A ) LENGTH: 67 amino acids
        ( B ) TYPE: amino acid
        ( D ) TOPOLOGY: linear ( x i ) SEQUENCE DESCRIPTION: SEQ ID NO:14:

```
Lys Glu Leu Arg Cys Gln Cys Ile Lys Thr Tyr Ser Lys Pro Phe His
 1               5                  10                  15

Pro Lys Phe Ile Lys Glu Leu Arg Val Ile Glu Ser Gly Pro His Cys
            20                  25                  30

Ala Asn Thr Glu Ile Ile Val Lys Leu Ser Asp Gly Arg Glu Leu Cys
        35                  40                  45

Leu Asp Pro Lys Glu Asn Trp Val Gln Arg Val Val Glu Lys Phe Leu
    50                  55                  60

Lys Arg Ala
65
```

HUMAN INTERLEUKIN-8 ANALOGS

RELATED APPLICATIONS

The present application is a U.S. national phase application of PCT/CA92/00528, filed 3 Dec. 1992, which is a continuation in part of U.S. Ser. No. 07/801,578, filed 4 Dec. 1991, abandoned.

TECHNICAL FIELD

This invention relates to the human cytokine, interleukin-8.

BACKGROUND OF THE INVENTION

A human cytokine that promotes the recruitment and activation of neutrophil leukocytes has been identified as one of several endogenous mediators of the acute inflammatory response. In the past it was variously termed neutrophil-activating factor, monocyte-derived neutrophil chemotactic factor, interleukin-8 (IL-8), and neutrophil-activating peptide-1. IL-8 appears to have gained the widest acceptance and the term will be used herein.

The most abundant naturally occurring form of the IL-8 monomer is a 72-residue protein apparently derived by processing of a 99-residue precursor. Other proteins with related sequences, including neutrophil-activating peptide-2 and GRO$\alpha$ (with melanoma growth stimulatory activity) are IL-8 homologues which have neutrophil-activating properties.

The in vitro effects of IL-8 on neutrophils are similar to those of other chemotactic agonists such as C5a and fMet-Leu-Phe and include induction of a transient rise in cytosolic free calcium, the release of granules containing degradative enzymes such as elastase, the respiratory $H_2O_2$ burst, neutrophil shape change, and chemotaxis. IL-8 appears to bind to at least one class of receptor sites on neutrophils with a frequency of approximately 64,000/cell and a $K_d$ of 0.2 nM.

The three-dimensional structure of IL-8 is known by two-dimensional NMR and x-ray diffraction techniques. The IL-8 monomer has antiparallel $\beta$ strands followed by a single overlying COOH-terminal $\alpha$ helix. Two disulfide bridges, between cysteines 7 and 34, and between cysteines 9 and 50 seem to stabilize the tertiary structure. Residues 1–6 and the loop residues 7–18 seem to have little defined secondary structure. In solution, IL-8 is a noncovalent homodimer which is stabilized primarily by interactions between the $\beta$ strands of the two monomers.

Examination of the three-dimensional structure indicates that following the cysteine at position 50, the residues form a type 1 $\beta$ turn (at residues 51 to 55) followed by an amphipathic $\alpha$ helix (at residues 55 to 72) that transverses the $\beta$ sheet. The hydrophobic face of the $\alpha$ helix interacts with and stabilizes the hydrophobic face of the $\beta$ sheet. Some of the interactions are between the two subunits of the dimeric molecule.

As it is established that IL-8 is a key mediator of inflammatory diseases, it would be desirable to identify substances capable of blocking or interrupting the activity of IL-8 for use in anti-inflammatory compositions. Such compositions may prove to be advantageous over presently available steroid based anti-inflammatory drugs which often have severe side-effects with the continued usage that is required for chronic inflammatory diseases. It would also be desirable to identify IL-8 analogs having an increased inflammatory activity for medical research applications.

The investigation described herein arose as a result of an investigation of the functioning of the IL-8 cytokine carried out by production of structural analogs of IL-8.

IL-8 has been previously produced through chemical synthesis (for example see: Clark-Lewis, et al "Chemical Synthesis, Purification, and Characterization of Two Inflammatory Proteins; Neutrophil-Activating Peptide-1 (Interleukin-8) and Neutrophil-Activating Peptide-2" (1991) Biochemistry 30: 3128–3135) and by recombinant DNA methods (for example see: Hebert, et al "Scanning Mutagenesis of Interleukin-8 Identifies A Cluster of Residues Required for Receptor Binding" (1991) J. Biol. Chem. 286: 18989–18994). Such methods of synthesis make it possible to produce analogs of IL-8 in order to investigate such aspects of the cytokine as the receptor binding site(s). In addition, it is known that IL-8 exists in several forms that vary at the $NH_2$-terminus, which have been detected in preparations purified from natural sources. These variations correspond to the predominant 72-residue form (which is generally considered to be the prototype IL-8 molecule); a 77-residue form having 5 additional $NH_2$-terminus amino acids on each monomer; and, two shortened forms having residues 3–72 and 4–72 of the 72 amino acid form, respectively.

SUMMARY OF THE INVENTION

The inventors' herein have investigated several structural analogs of IL-8 and have discovered that manipulation of the 72-residue form of IL-8, particularly in the N-terminal region thereof, yields IL-8 analogs having therapeutically useful properties. More particularly, the IL-8 analogs of the present invention comprise an amino acid sequence substantially equivalent to the IL-8 sequence beginning at residue 4 and continuing at least to residue 51, wherein at least one of the N-terminal residues found to be critical for neutrophil binding and stimulation, i.e., $Glu^4$-$Leu^5$-$Arg^6$, is either replaced or deleted.

In embodiments of the invention, the $Glu^4$-$Leu^5$-$Arg^6$ region of IL-8 is modified selectively to provide antagonists of IL-8. In one particular embodiment, antagonists that compete strongly with IL-8 for neutrophil binding are obtained by replacing or deleting at least residue $Leu^5$. In another particular embodiment, antagonists that compete only weakly with IL-8 yet still retain antagonist properties are obtained by replacing at least residue $Arg^6$.

This invention also provides pharmaceutical compositions of the aforementioned analogs, comprising the analog and a suitable carrier therefor. Also provided are methods of the use of the aforementioned analogs.

IL-8 analogs having the first 2 or 3 residues at the $NH_2$-terminus of the 72-residue monomer deleted so as to provide the 3–72 and 4–72 forms are useful as enhanced inflammatory mediators. It has now been found that C-terminally truncated analogs of IL-8 (3–72) and IL-8 (4–72) have significant biological activity.

Accordingly, this invention also provides a biologically active human interleukin-8 (IL-8) analog having an amino acid sequence substantially equivalent to the IL-8 1–72 sequence beginning at residue 4 and continuing to a COOH-terminus at residue 51 or a residue between residue 51 and residue 72. This invention also provide the preceding analog that additionally comprises residue 3 of IL-8 1–72 or additionally comprises residues 1–3 of IL-8 1–72.

This invention also provides pharmaceutical compositions comprising the aforementioned biologically active analogs together with a suitable carrier therefor.

The invention also provides methods of use of the aforementioned analogs. In addition, this invention also provides methods of use of IL-8 3–72 and IL-8 4–72 to activate human neutrophils and pharmaceutical compositions suitable therefor.

BRIEF DESCRIPTION OF THE DRAWINGS

For better understanding of the invention, reference may be made to the preferred embodiments and examples described below, and the accompanying drawings, in which.

Shown are determinations at the indicated concentrations of IL-8 1–72: ●1–72; ▲, 3–72; △, 4–72; ◊, 5–72; ■, 6–72; □, 7–72; and o, 77-residue IL-8. Unidirectional error bars indicate the standard deviations. Data are representative of three assays using different neutrophil preparations.

Figure 1:
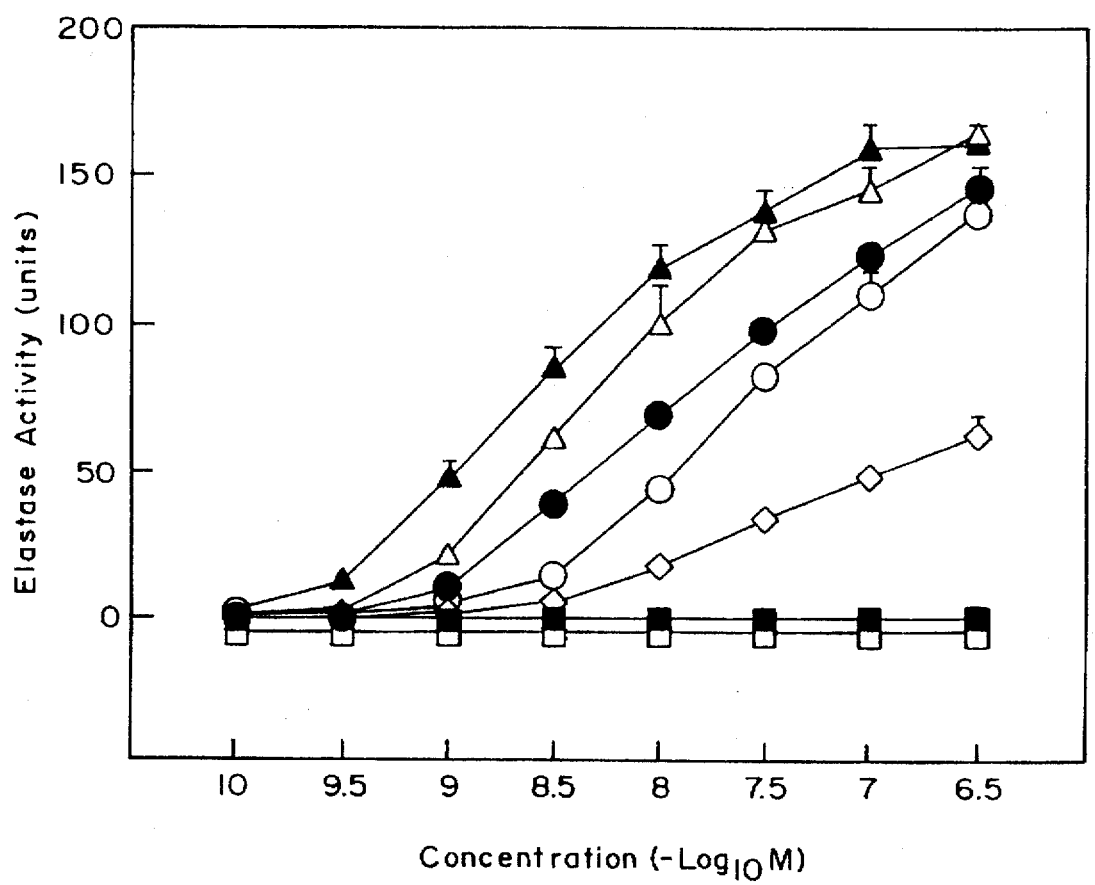
FIG. 1 is a graph showing neutrophil elastase release activity of NH-terminal deletion IL-8 analogs.
Figure 2:
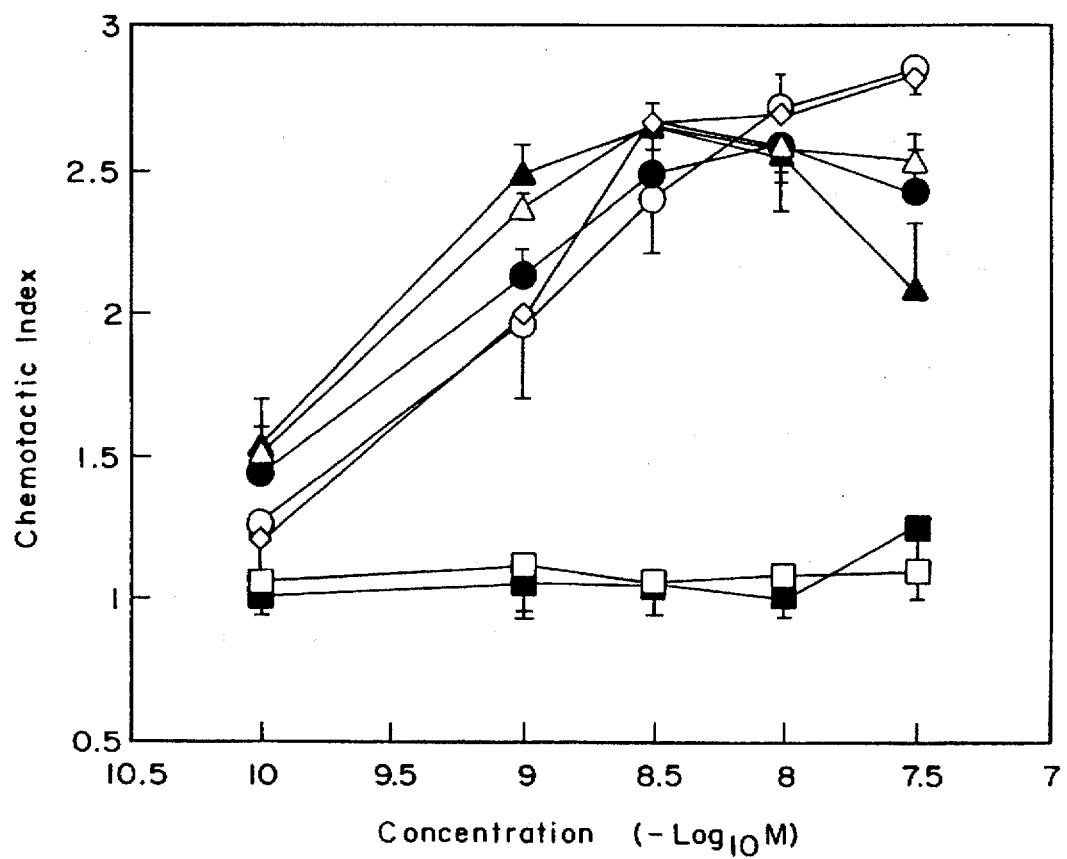

FIG. 2 is a graph showing neutrophil chemotaxis activity of NH$_2$-terminal deletion IL-8 analogs. The chemotaxis index (stimulated migration/control random migration) was determined at the indicated concentrations of IL-8 1–72: ● 1–72; ▲, 3–72; △, 4–72; ◊, 5–72; ■, 6–72; □, 7–72; and o, 77-residue IL-8. Unidirectional error bars indicate the standard deviations. Data are representative of three assays using different neutrophil preparations.

Figure 3:
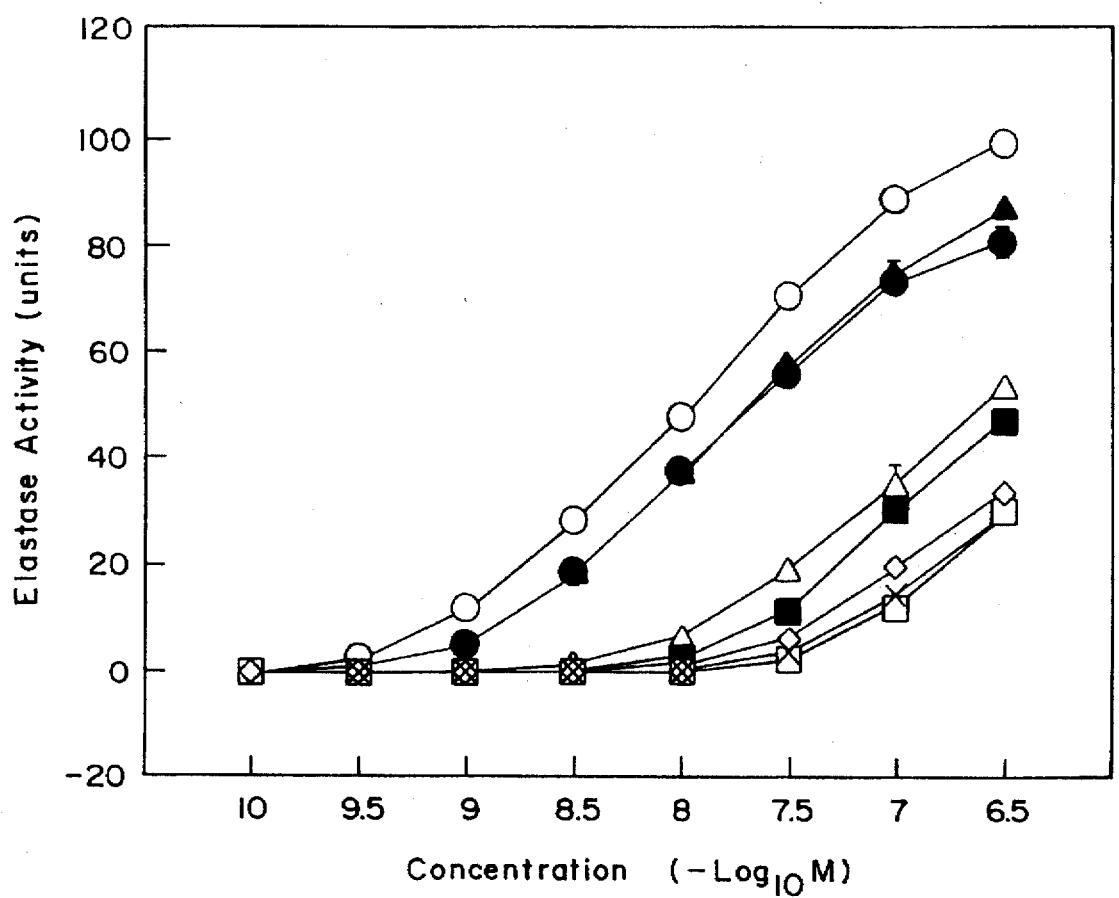

FIG. 3 is a graph showing neutrophil elastase release activity of COOH-terminal deletion IL-8 analogs. Shown are determinations at the indicated concentrations of IL-8 1–72: ●1–72; o, 1–69; ▲, 1–66; △, 1–63; ■, 1–60; □, 1–58; ◊, 1–54; and X, 1–51. Unidirectional error bars indicate the standard deviations. Data are representative of three assays using different neutrophil preparations.

Figure 4:
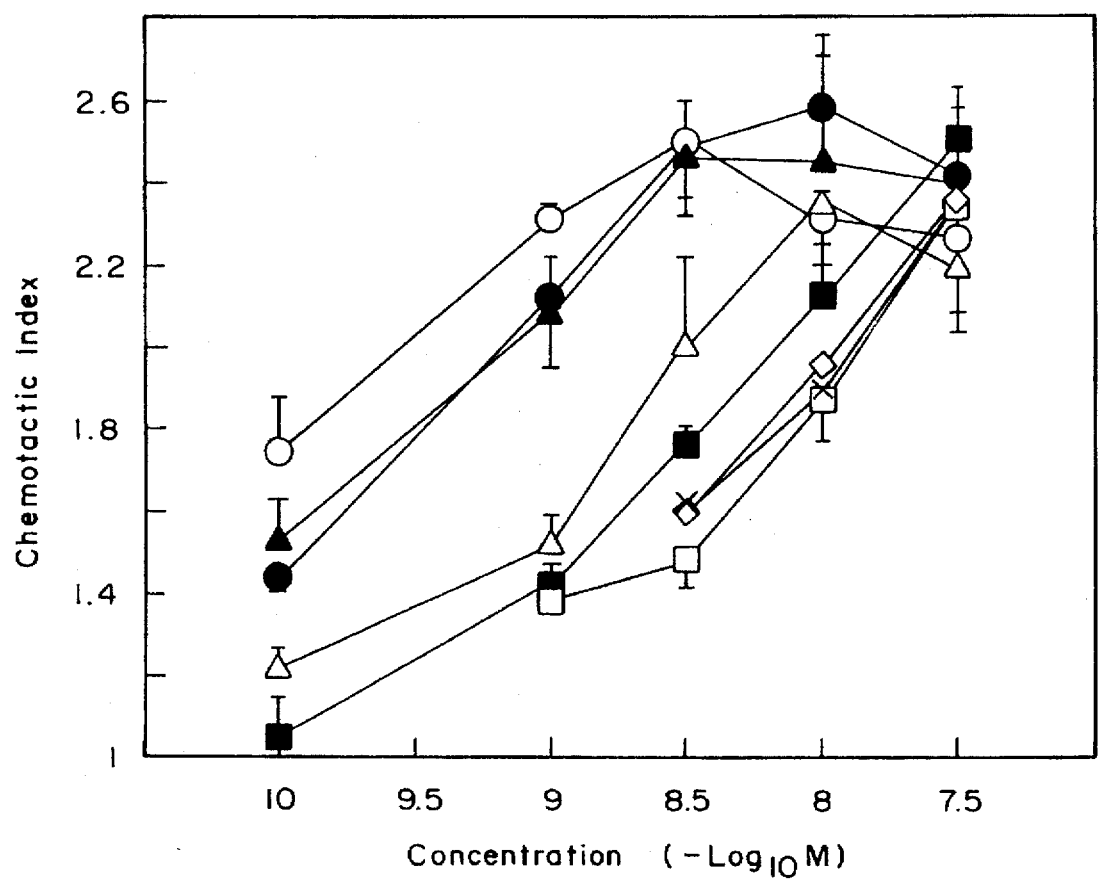

FIG. 4 is a graph showing neutrophil chemotaxis activity of the COOH-terminal deletion IL-8 analogs. The chemotactic index (stimulated migrations/control random migration) was determined at the indicated concentrations of IL-8 1–72: ●1–72; o, 1–69; ▲, 1–66; △, 1–63; ■, 1–60; □, 1–58; ◊, 1–54; and X, 1–51. Unidirectional error bars indicate the standard deviations. Data are representative of three assays using different neutrophil preparations.

Figure 5:
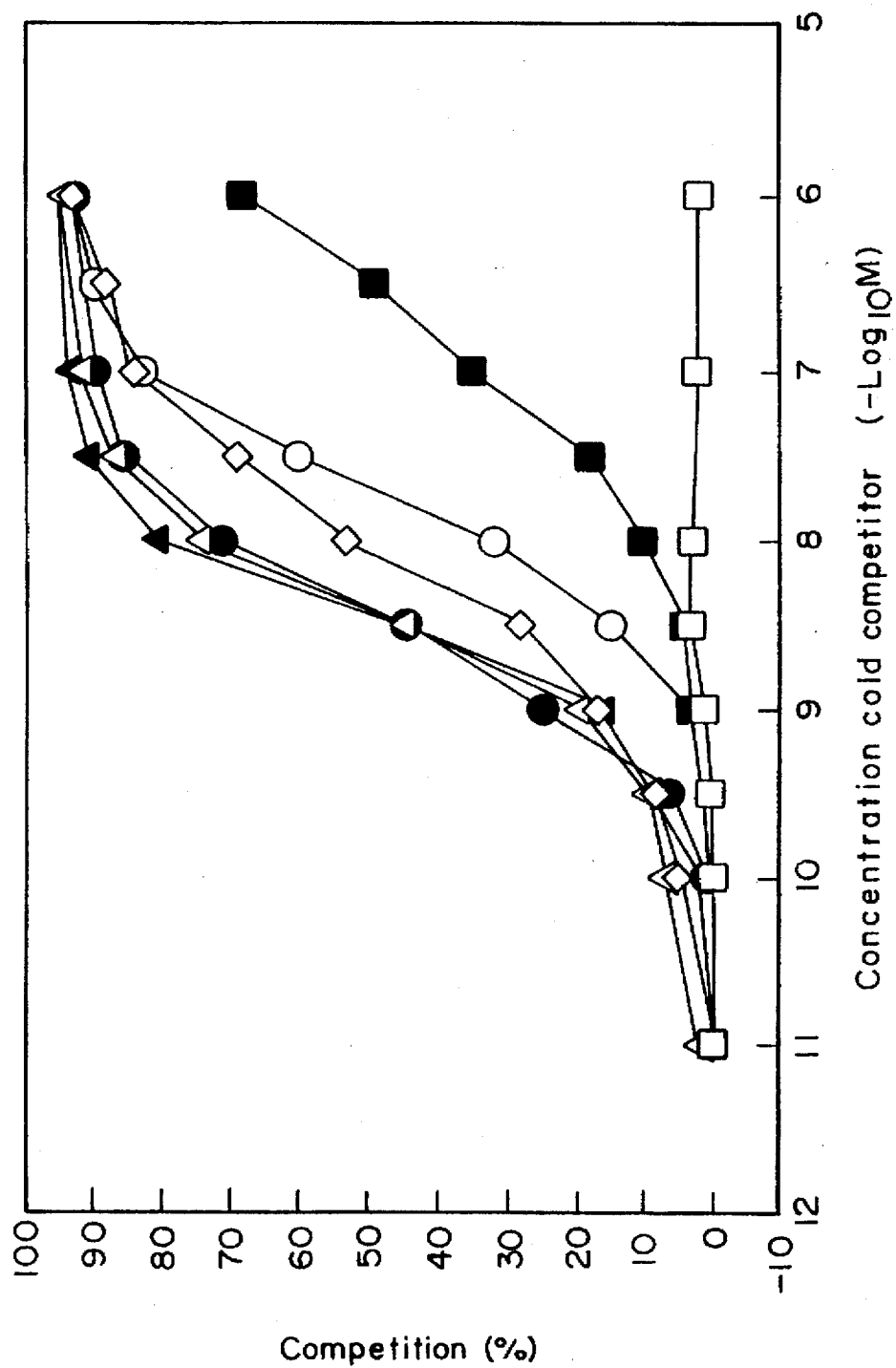

FIG. 5 is a graph showing competitive binding of the NH$_2$-terminal deletion IL-8 analogs to neutrophils. The percentage of specific $^{125}$I-labelled IL-8 1–72 counts competed from purified neutrophils were calculated after subtraction of nonspecific binding. Shown are determinations at the indicated concentrations of IL-8 1–72: ●1–72; ▲, 3–72; △, 4–72; ◊, 5–72; ■, 6–72; □, 7–72; and o, 77-residue IL-8.

Figure 6:
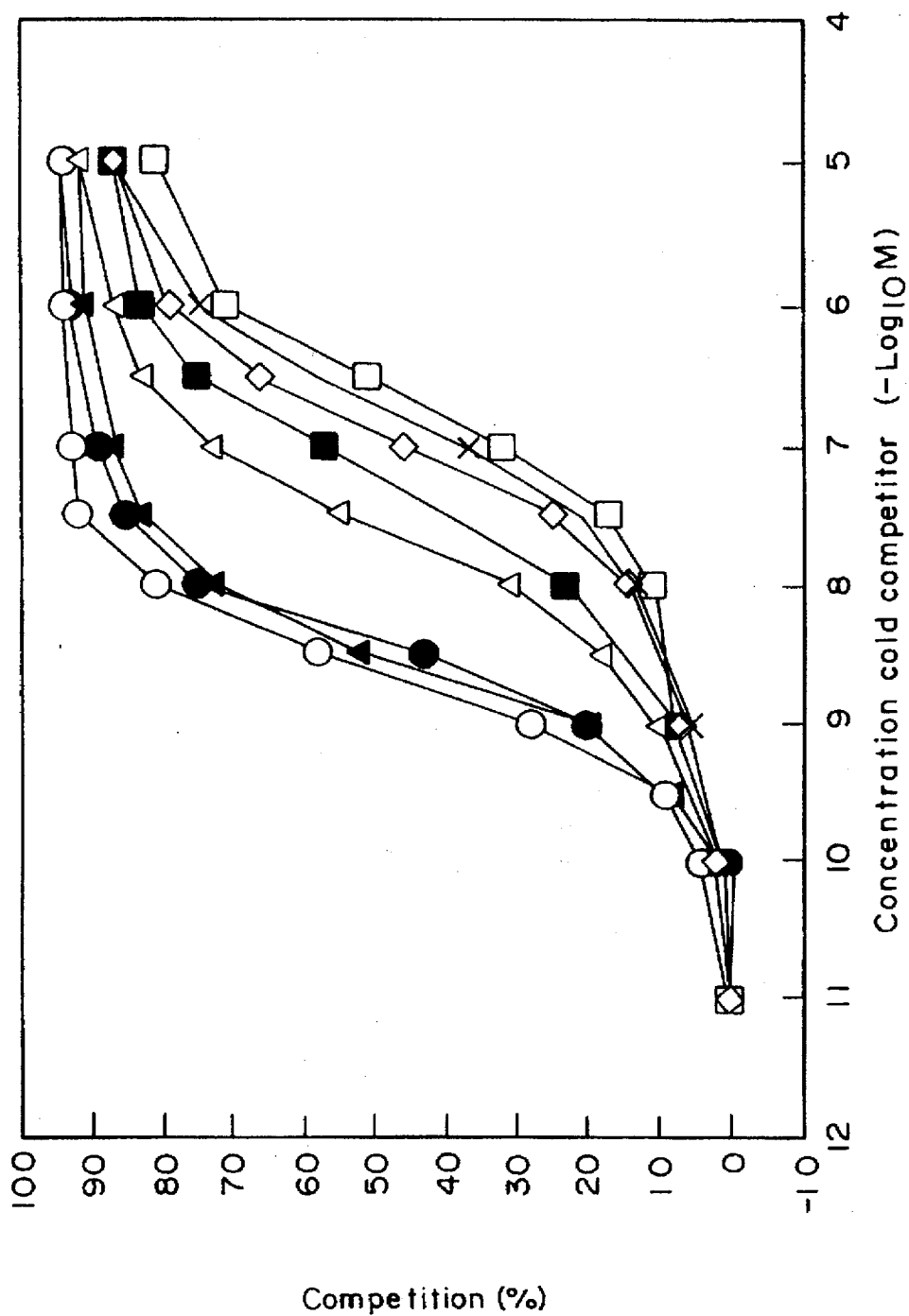

FIG. 6 is a graph showing competitive binding of the COOH-terminal deletion IL-8 analogs to neutrophils. The percentage of specific $^{125}$I-labelled IL-8 1–72 counts competed from purified neutrophils were calculated after subtraction of nonspecific binding. Shown are determinations at the indicated concentrations of IL-8 1–72: ●1–72; o, 1–69; ▲, 1–66; △, 1–63; ■, 1–60; □, 1–58; ◊, 1–54; and X, 1–51.

Figure 7:
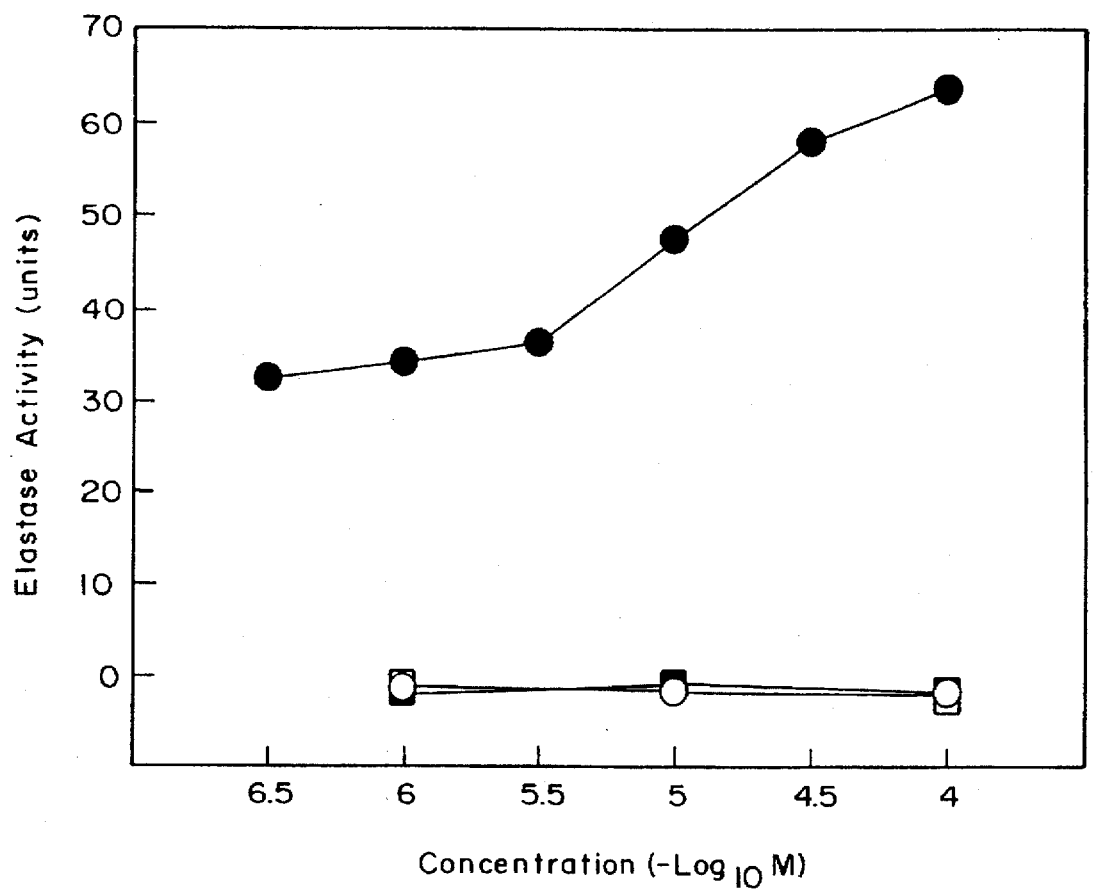

FIG. 7 is a graph showing neutrophil elastase release activity and synergistic activity of NH- and COOH-terminal IL-8 peptides. Shown are determinations at the indicated concentrations of the NH-terminal peptide corresponding to residues 1–10 of 77-residue IL-8 (■), the COOH-terminal peptide corresponding to residues 51–72 of IL-8 (□), and the indicated concentrations of the NH$_2$-terminal peptide with $10^{-7}$M IL-8 6–72 (o), and the COOH-terminal peptide with $10^{-7}$M of IL-8 1–51 (●).

Figure 8:
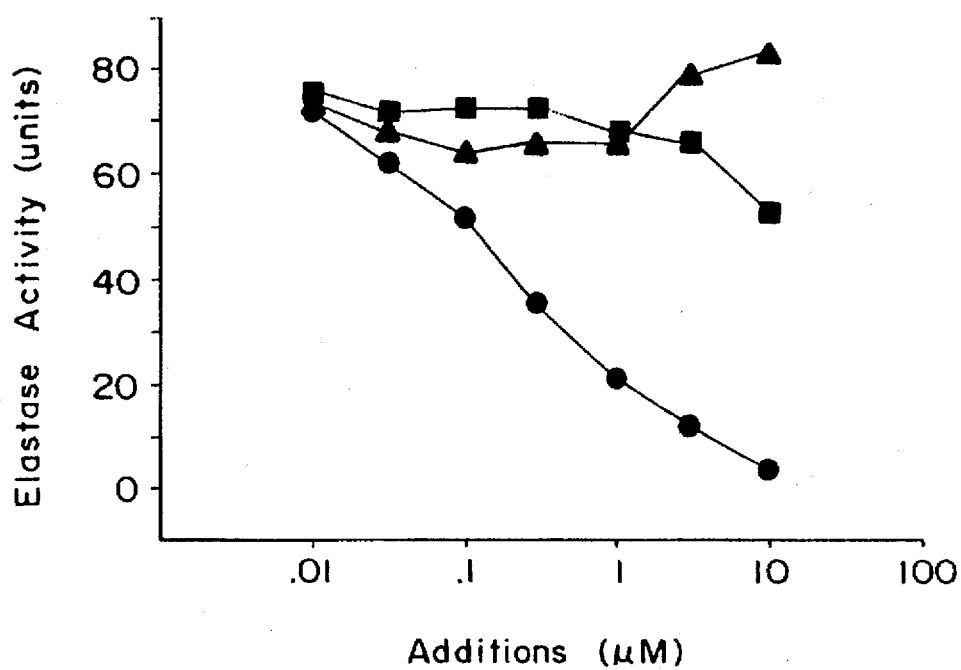

FIG. 8 is a graph showing elastase release by human neutrophils stimulated with IL-8 1–72 in the presence of increasing concentrations of IL-8 5–72 (▲), IL-8 6–72 (●and IL-8 7–72 (■).

Figure 9:
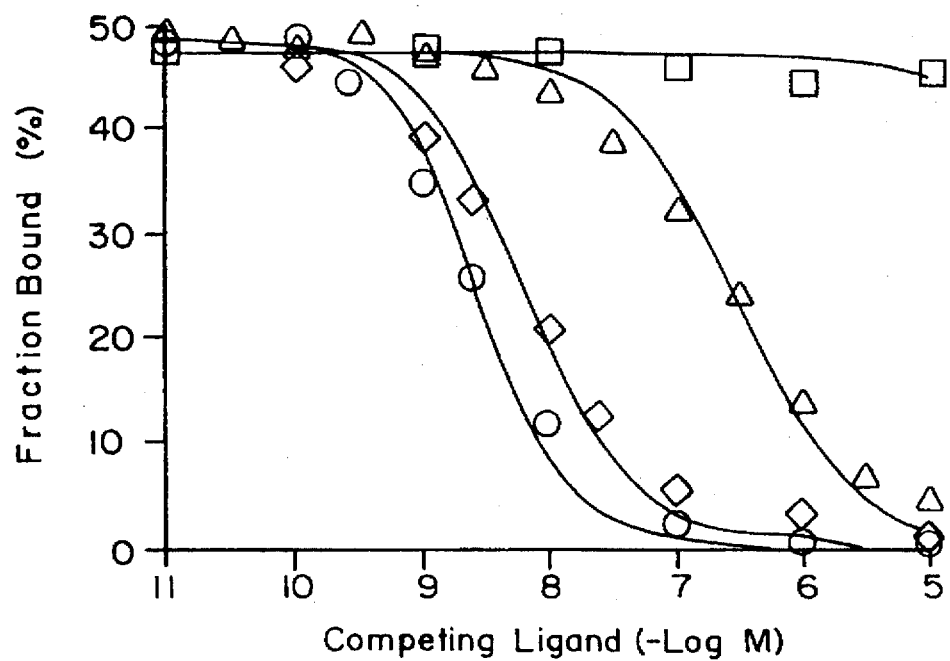

FIG. 9 is a graph showing the results of a competitive binding study with neutrophils incubated with labelled IL-8 1–72 in the presence of increasing concentrations of unlabelled IL-8 1–72 (o), IL-8 5–72 (◊), IL-8 6–72 (△), and IL-8 7–72 (□).

Figure 10:
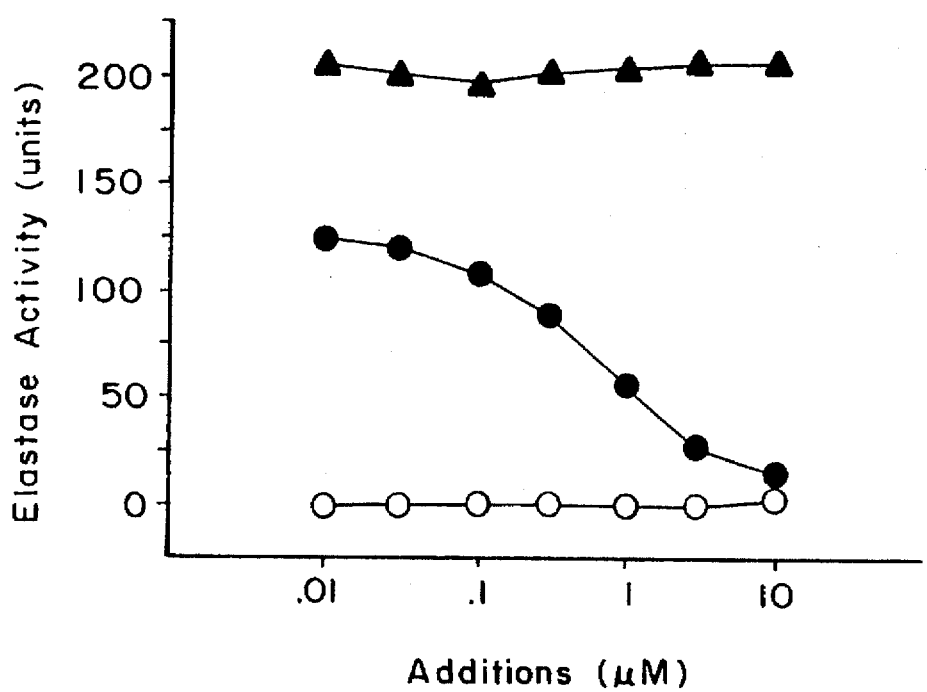

FIG. 10 is a graph showing elastase release by neutrophils stimulated with IL-8 1–72 (■) and Fmet-Leu-Phe (▲) in the presence of increasing concentrations of IL-8 6–72 and, the effect of IL-8 6–72 alone (o).

Figure 11:
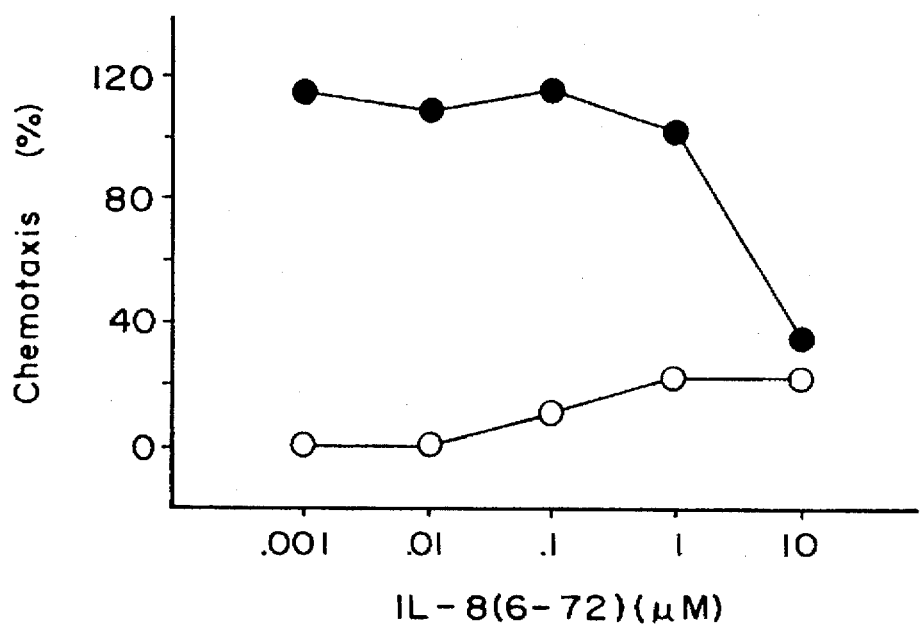

FIG. 11 is a graph showing neutrophil chemotaxis migration in the presence of IL-8 6–72 and IL-8 1–72 (● and, in the presence of IL-8 6–72 alone (o).

Figure 12:
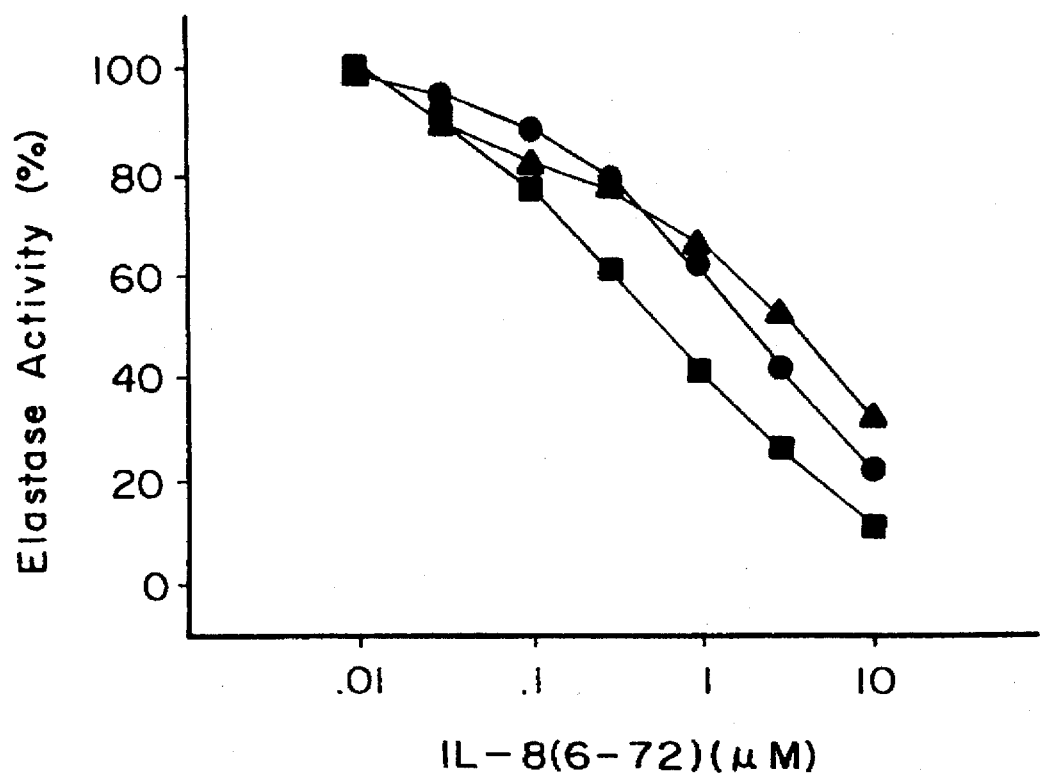

FIG. 12 is a graph showing elastase release by neutrophils stimulated with IL-8 (●; GROα (■) and NAP-2 (▲) in the presence of increasing concentrations of IL-8 6–72.

Figure 13A:
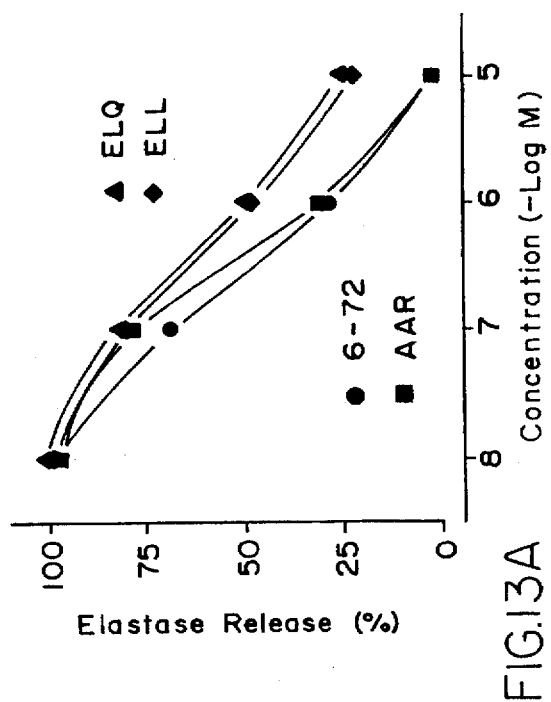
Figure 13B:
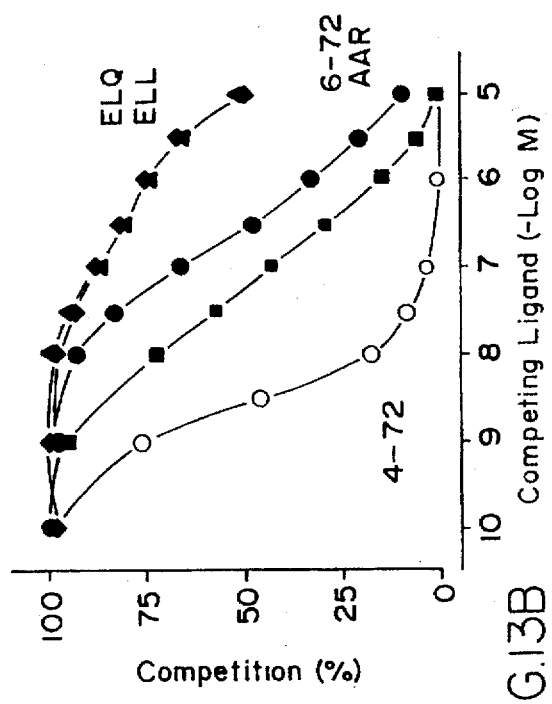
Figure 13C:
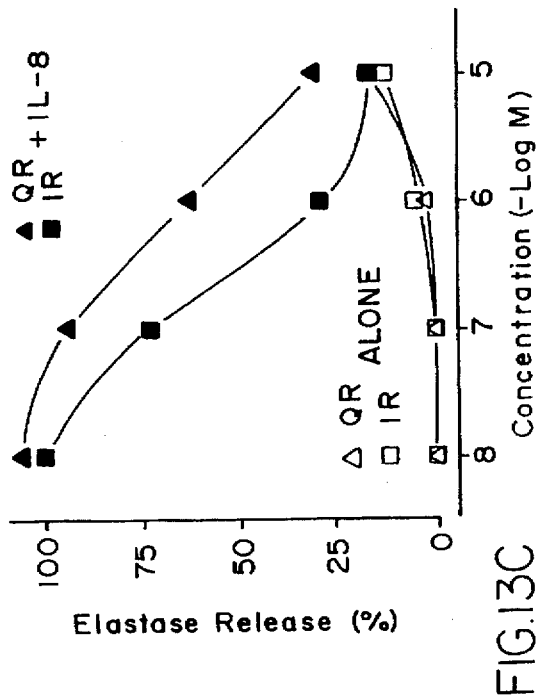
Figure 13D:
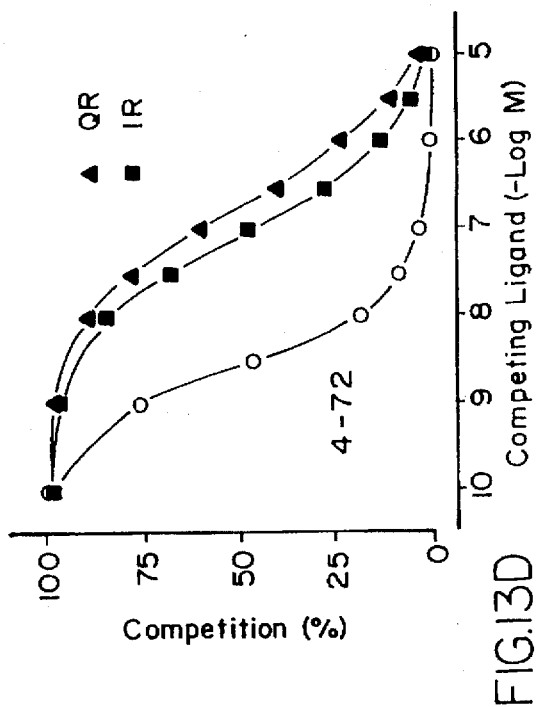
Figure 14A:
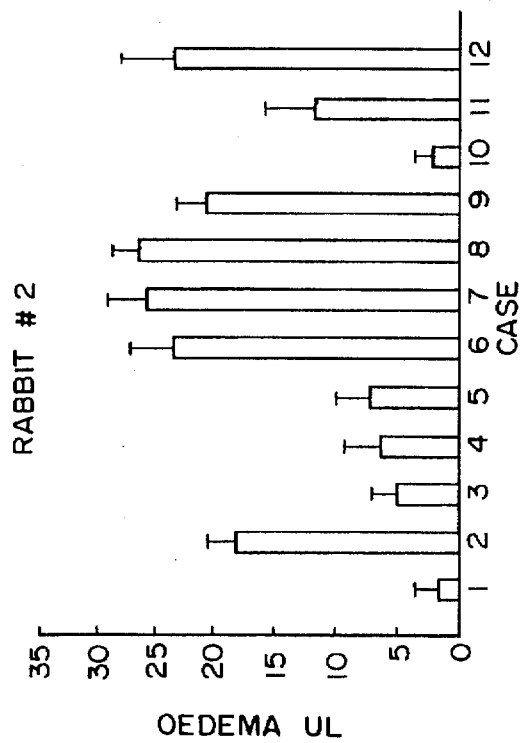
Figure 14B:
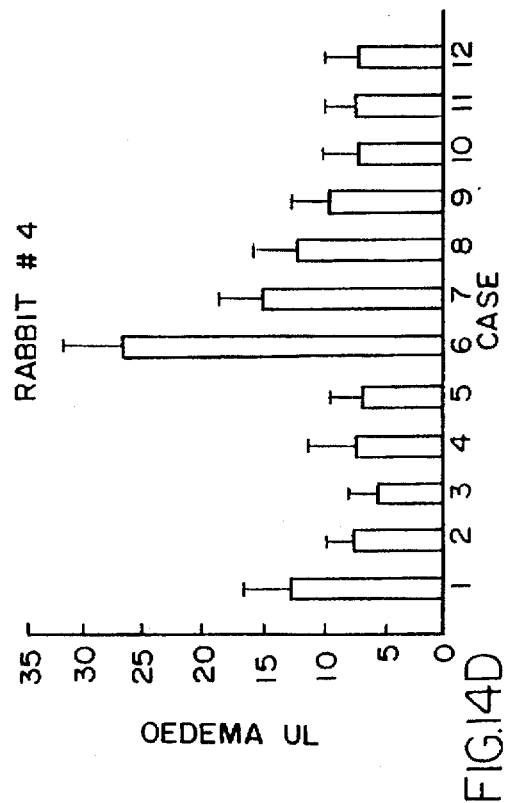
Figure 14C:
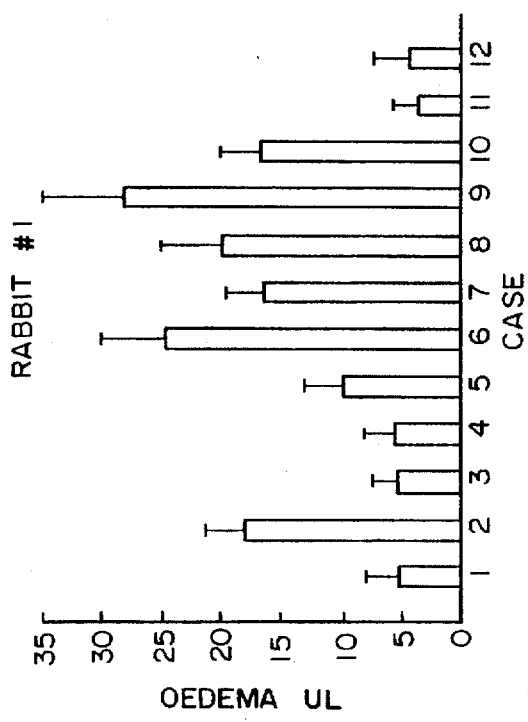
Figure 14D:
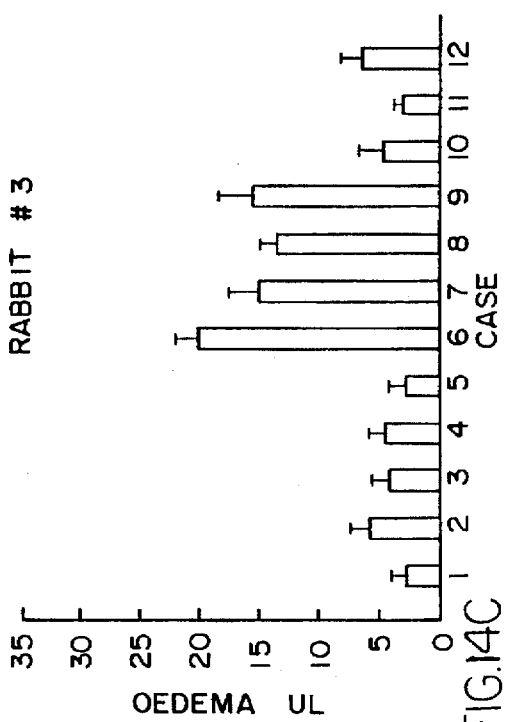
Figure 15A:
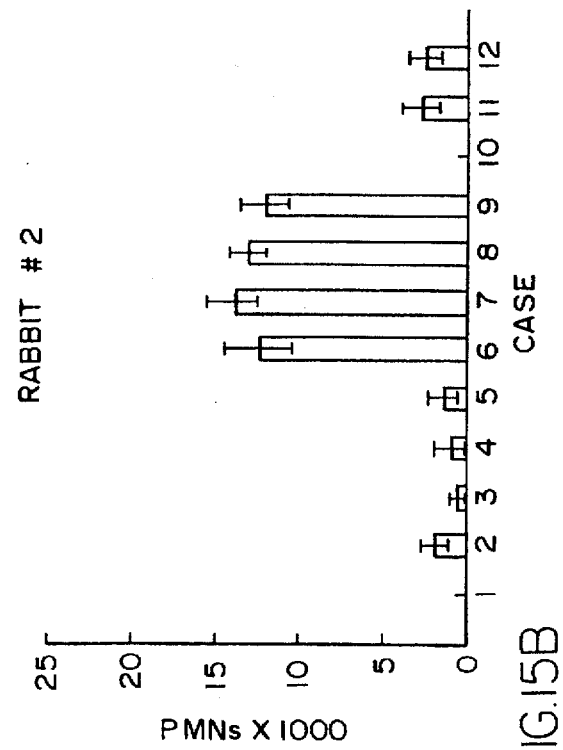
Figure 15B:
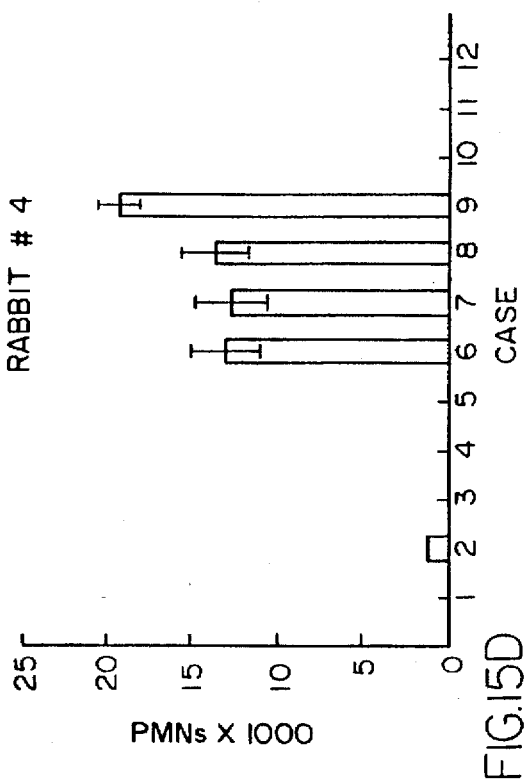
Figure 15C:
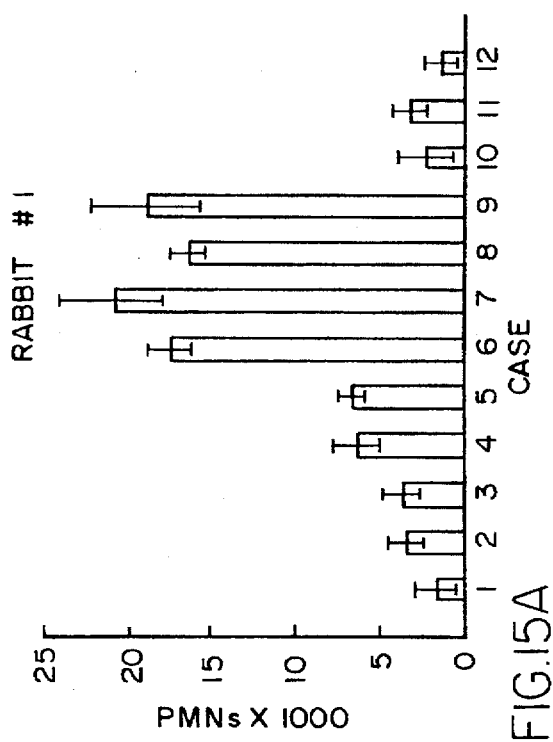
Figure 15D:
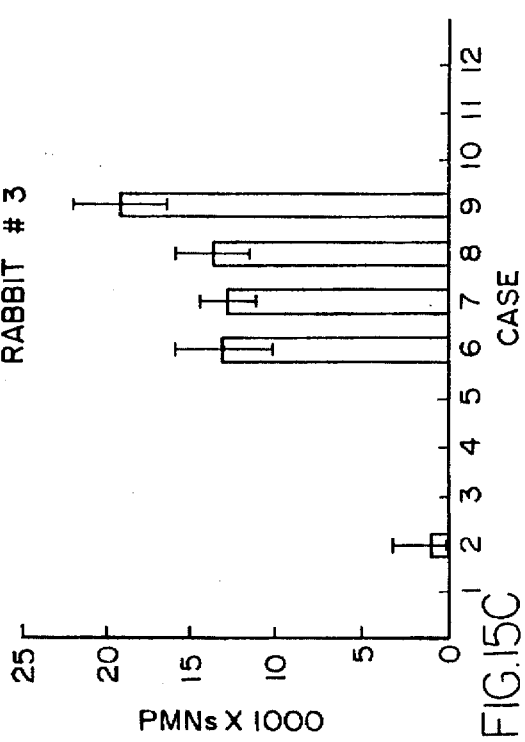

FIGS. 13A–13D provide graphs showing elastase release by neutrophils induced with 10 nM IL-8 (4–72) (FIGS. 13A and 13C); and competition for $^{125}$I-IL-8 binding to human neutrophils. Analogs used were IL-8, AAR (7–72) (■), IL-8, ELQ (7–72) (▲), IL-8, ELL (7–72) (♦), IL-8 (6–72) (● (FIGS. 13A and 13B), and IL-8, IR (7–72) (■), and IL-8, QR (7–72) (▲) (FIGS. 13C and 13D). Agonistic effects of IL-8, IR (7–72) (□) and IL-8, QR (7–72) (△) at high concentrations (FIG. 13C) as well as the competition by unlabelled IL-8 (4–72) (o) are also shown.

FIGS. 14 and 15 respectively show oedema and PMN accumulation responses in 4 separate experiments with 6 replicates for each injection; mean I s.e.m. for each rabbit. In each case identified by a numeral from 1–12, the injections are (1) PBS (vehicle); (2) IL-8 $1 \times 10^{-11}$ moles/site; (3) IL-8 $1 \times 10^{-11}$+AAR7–72 $1 \times 10^{-11}$ moles/site; (4) IL-8 $1 \times 10^{-11}$+AAR7–12 $1 \times 10^{-10}$ moles/site; (5) IL-8 $1 \times 10^{-11}$+ 6–72 $1 \times 10^{-10}$ moles/site; (6) IL-8 $1 \times 10^{-10}$ moles/site; (7) IL-8 $1 \times 10^{-10}$+AAR7–72 $1 \times 10^{-11}$ moles/site; (8) IL-8 $1 \times 10^{-10}$+AAR7–72 $1 \times 10^{-10}$ moles/site; (9) IL-8 $1 \times 10^{-10}$+IL-8 6–72 $1 \times 10^{-10}$ moles/site; (10) AAR7–72 $1 \times 10^{-11}$ moles/site; (11) AAR7–72 $1 \times 10^{-10}$ moles/site; (12) 6–72 $1 \times 10^{-10}$ moles/site.

DESCRIPTION OF THE PREFERRED EMBODIMENTS

The 72-residue form of the IL-8 monomer from the NH$_2$-terminus to the COOH-terminus is as follows:

SEQ ID NO: 1

Ser Ala Lys Glu Leu Arg Cys Gln Cys Ile Lys Thr Tyr Ser Lys
                5                    10                  15
Pro Phe His Pro Lys Phe Ile Lys Glu Leu Arg Val Ile Glu Ser
                20                    25                  30
Gly Pro His Cys Ala Asn Thr Glu Ile Ile Val Lys Leu Ser Asp
                35                    40                  45
Gly Arg Glu Leu Cys Leu Asp Pro Lys Glu Asn Trp Val Gln Arg
                50                    55                  60
Val Val Glu Lys Phe Leu Lys Arg Ala Glu Asn Ser
                65                    70

Throughout this specification, reference to residue numbers in IL-8 analogs will be a reference to the numbered residues shown above. For example, when the first 2, 3, 4 or 5 residues at the NH$_2$-terminus are deleted, the analogs will be referred to as the 3–72, 4–72, 5–72, and 6–72, forms respectively. Replacement amino acids in the IL-8 analogs will be referred to by their identity and location within the sequence shown above. Thus, an analog of IL-8 (4–72) in which the Arg residue at position 6 is replaced with Ile, for instance, will be referred to as Glu$_4$Leu$^5$Ile$^6$(7–72) or, more simply by single letter code, as ELI (7–72). Such forms may be prefixed with the term IL-8 as a complete denomination. Other analogs will be referred to by similar notations with reference to the above 72-residue sequence.

With reference to the sequence shown above, IL-8 analogs of the present invention may comprise an amino acid sequence that is either identical to the illustrated sequence, or to a region thereof as herein defined, or may comprise an amino acid sequence that is "substantially equivalent" thereto. Sequences that are "substantially equivalent" are characterized by from 1 to 10, e.g. up to 5, amino acid deletions or replacements that do not cause a statistically significant change in the activity of the analog, relative to a counterpart comprising an amino acid sequence identical to the sequences shown above. Whether a change in activity resulting from an amino acid change or deletion is statistically significant will of course be determined in the context of the assay used to identify the given activity. Known three-dimensional modelling techniques may be used to design and construct further analogs of this invention wherein conservative alterations are made within the core sequences described above which will not prevent the analog from binding to the neutrophil. It is expected that many such conservative alterations may be made, particularly in the C-terminal region beyond residue 35. In making such modifications it is expected that it will be necessary to retain the characteristic disulfide bridges of the IL-8 monomer. For example, replacement of Cys 9 and Cys 50, or Cys 7 and Cys 34 with amino butyric acid (ABA) in IL-8, results in a loss of elastase release activity.

Specific amino acid replacements that may be tolerated include: Lys 15→Arg; Tyr 13→Phe; Ile 10→Val; His 33→Ala; His 33→Glu; His 33→Gln; His 33→Ser; Ser 14→Thr; Thr 12→Ser; Lys 11→Arg; Gln 8→Leu; Arg 26→Glu; Lys 23→Glu; Glu 29→Lys, since these substitutions in IL-8 do not significantly affect elastase release activity.

The IL-8 analogs of this invention may be synthesized chemically by a variety of known means or according to the specific examples herein. The analogs may also be synthesized by a variety of known recombinant DNA techniques such as those described by Hebert, et al (1991) [supra]; Hebert, et al (1990) J. Immunol. 145: 3022–3040; or, Lindley, et al (1988) Proc. Natl. Acad. Sci. U.S.A. 85: 9199–9203. To produce the analogs described herein it is only necessary to delete or replace the codons in the nucleic acid sequences employed that correspond to the amino acid residues that are to be replaced or deleted.

Cytokine analogs of IL-8 are formed by permitting the analog monomers to fold and associate in the dimer form. Folding is accomplished by permitting the formations of the disulfide bridges by oxidation of the appropriate half cysteines, for example by the procedures described in Clark-Lewis, et al (1988) Proc. Natl. Acad. Sci. U.S.A. 85: 7897–7902; Woo, et al (1989) Protein Eng. 3: 39–37; and Clark-Lewis, et al (1991) [supra]. The monomers will spontaneously associate by hydrogen bonding in solution.

As will be described below in further detail, IL-8 biological activity is retained when certain COOH-terminal residues are deleted but potency is progressively reduced as the COOH-terminal residues are excluded. Some activity is retained in a 1–51 residue analog wherein the entire COOH-terminal α and β turns are missing. For biological activity, it is preferred that the deletions be only of the COOH-terminal residues in the region 67–72 as a significant amount of biological activity is shown to be retained by the IL-8 1–66 analog and enhanced activities are demonstrated in the 1–69 analog. In the preferred analogs which provide enhanced neutrophil activation, the $NH_2$-terminus will be either the 3rd or 4th residue and the sequence of the monomer will continue to a desired COOH-terminus, preferably in the area of residues 66–72. Analog 1–69 also has potent biological activities.

For IL-8 mediators with low neutrophil activation activity and strong chemotaxis activity, the preferred analogs are derived from the 5–51 form as a core sequence, preferably with further COOH-terminus residues being present, and most preferably with the COOH-terminus being residue 66–72.

In a valuable aspect of the present invention, there are provided IL-8 analogs that are antagonists of IL-8 activity. Antagonists of IL-8 activity are characterized by the ability to reduce one or more of the measurable consequences of IL-8-mediated neutrophil stimulation. Biological assays are known which may be used to test for IL-8 activities or an ability to block or inhibit IL-8. The in vitro assays require human neutrophils which may be isolated from donor blood by known procedures such as that described by Peveri, et al (1988) J. Exp. Med. 167: 1547–1559. The assays include measurement of elastase release, cytosolic free calcium changes, and chemotaxis and may be performed according to methods described by Schroder, et al (1987) J. Immunol. 139: 3474–3483; and, Peveri, et al (1988) [supra].

Analogs of IL-8 having IL-8 antagonist activity may be further characterized by their ability to compete with IL-8 for neutrophil binding. Analogs that compete relatively strongly exhibit a Kd value that is less that about 50 nM, as determined using the assays herein described. According to embodiments of the invention, IL-8 analogs that have IL-8 antagonist activity and compete relatively strongly with IL-8 for neutrophil binding comprise an amino acid sequence substantially equivalent to IL-8(4–72), wherein the $Glu^4$-$Geu^5$-$Arg^6$ region is modified to confer on the analog a Kd value of less than about 50 nM. Modifications suitable for this purpose include deletion of $Glu^4$ and replacement of $Glu^4$ and/or $Leu^5$. Replacement amino acids may be selected from among any of the naturally occurring and synthetic amino acids, including but not limited to amino acids having a hydrophobic side chain. Specific replacement amino acids include alanine, isoleucine, glutamine and leucine. Preferred embodiments of the present invention include the following human IL-8 analogs: $Ala^4Ala^5$ (6–72); $Ile^5$ (6–72); $Gln^5$ (6–72); and (6–72).

Analogs that compete relatively weakly with IL-8 for neutrophil binding yet exhibit relatively strong antagonistic activity, as determined in the elastase release assay, are also provided by the present invention. This remarkable combination of characteristics has surprisingly also been found in IL-8 analogs comprising an amino acid sequence substantially equivalent to IL-8 (4–72), wherein the $Glu_4$-$Leu^5$-$Arg^6$ region is modified to confer on the analog a Kd value of greater than about 50 nM. Modifications capable of yielding analogs of this type include replacement of the $Arg^6$ residue. Replacement amino acids may be selected from the naturally occurring and synthetic amino acids, including but not limited to those having a hydrophobic side chain. Specific replacement amino acids include leucine, norleucine (Nle) and lysine. Preferred embodiments of the present invention include the following human IL-8 analogs: $Glu^4Leu^5Leu^6$ (7–72); $Glu^4Leu^5Nle^6$ (7–72); and $Glu^4Leu^5Lys^6$ (7–72).

For IL-8 antagonists, preferred analogs are derived from at least the 6–51 form as a core sequence with further COOH-terminus residues being optionally present, up to and including residue 72.

Methods of in vitro use of the analogs of this invention either to bring about neutrophil activation or to block the effects of IL-8 or similar compounds on neutrophils will be readily apparent from the examples herein. In addition, methods of in vivo use, particularly in humans, will be readily apparent to those skilled in the art. To limit inflammation in humans, one or more of the antagonists may be administered, for example through intravenous injection, inhalation, or by oral administration, particularly when formulated with a suitable carrier in a pharmaceutical composition. The analogs which have IL-8 activity may be used to activate neutrophils. For example, cytokines of such analogs may be administered to an animal, particularly a human, in order to stimulate an inflammatory response. The analogs that bring about a strong chemotaxis activity such as the 5–72 form may be administered to attract neutrophils to an area of disease. For those cytokine analogs having a greater potency than IL-8 such as IL-8 3–72 and IL-8 4–72, inflammation response or neutrophil activation may be enhanced.

A combination of analogs or analogs and other peptides may be used. For example, the 1–51 analogs may be employed for its ability to bind to neutrophils but cause a low level of neutrophil activation; subsequently, the 51–72 peptide may then be used or administered to boost the neutrophil activating activity of the 1–51 analog.

The analog monomers of the invention may be synthesized according to the following protocol. A fully automated peptide synthesizer (Applied Systems 430A) is used. The synthesis is started with a protected C-terminal amino acid linked to a cross-linked polystyrene resin via a 4-(carboxamidomethyl)benzyl ester linkage (the so-called pam resin) (0.4 mmol of 0.8 mmol/g of aminoacyl resin). $N^\alpha$-t-Boc acids with appropriate side chain protecting groups are added in a stepwise fashion until the entire protected polypeptide chanin is formed. Side chain protection is as follows: benzyl (Asp, Gly, Ser, and Thr); 4-methylbenzyl (Cys); toluenesulfenyl (Arg); 2-chlorobenzyloxycarbonyl (Lys); 2-bromobenyloxycarbonyl (Tyr); formyl (Trp); dinitrophenyl (His); and none (Ala, Ash, Gly, Gln, Ile, Leu, Met, Phe, Pro, Val.). Samples may be taken after each step to retrospectively monitor the amino acid coupling yields using a ninhydrin-based reaction following the procedures of Sarin, et al (1981) Anal. Biochem. 117: 147–157. The protected polypeptide resin is treated twice for 30 min with 2-mercaptoethanol (20%) in dimethylformamide containing diisopropylethylamine (5%) to remove the DNP groups form the histidine side chains. The resin is dried and cleaved using the "low-high" hydrogen fluoride method as described by Tam, et al (1983) J. Am. Chem. Soc. 105: 6442–6485 except for the following modifications. After the 25% hydrogen fluoride step, the partially protected peptide resin is filtered from the reaction mixture by using an all-Teflon filtration apparatus fitted with a Zitex filter and washed with dichloromethane and dried before the high 90% hydrogen fluoride step. The ethyl acetate precipitate of the material released form the resin is dissolved in 50 ml of 6M guanidine hydrochloride, 0.1M Tris-acetate, pH 8.5, and 20% 2-mercaptoethanol and stirred at 37° C. for 2 h and then acidified with 2 mil of acetic acid. This mixture is the crude peptide product.

Alternately, histidine may be protected with π benzyloxymethyl instead of dinitrophenyl. The π benzyloxymethyl group is acid labile thus eliminating the need for thiolysis of the dinitrophenyl group before and after hydrogen fluoride deprotection. Acetylation is carried out on the $N^\alpha$ deprotected but otherwise fully protected peptide resin using acetic anhydride (10%) in dimethyl formamide.

The crude peptide product may be purified and folded according to the following protocol. Three different C-18 silica HPLC columns may be used in the purification and analysis of the peptide, including a preparative column (22.4×250 mm column with at 22.4×100 mm guard column) packed with 12 μm, 300-A pore size packing (Dynamax, Rainin Instrument Co., Woburn, Mass.); a semipreparative column (10×250 mm) Vydac C-18 column, with 5-μm particle, 300-A pore-size packing (Separations Group, Hesperia, Calif.); and an analytical column (4.6×250 mm) (Vydac) containing the same packing. The crude peptide product is loaded onto the preparative column and the retained material eluted with a 0–60% water-acetonitrile gradient in 0.1% trifluoracetic acid over 4 h at a flow rate of 15 ml/min. A sample (25 μl) of fractions containing 225-nm UV-absorbing material are rerun on the analytical column using reverse phase HPLC with the above described elution gradient run over 1 h. By comparison with the profile of the crude material, fractions containing the major peak are pooled and lyophilized. This material is reconstituted in 1M guanidine hydrochloride and Tris-acetate, pH 8.5, at a concentration of 0.2 mg/ml and stirred vigorously overnight in an open beaker so the air was kept bubbling through the mixture by vortex action. This procedure promotes formation of the disulfide bridges by oxidation of the appropriate half-cysteines. The material is acidified with 2 ml of acetic acid, and half was loaded onto the semipreparative column and the retained material eluted with the same gradient as described above at a flow rate of 3 ml/min. Samples of each fraction are run on the analytical column. Fractions containing only material with the retention time of the major peak in the folded material are pooled and lyophilized.

An assay for free sulfhydryls using Ellman reagents, as described by Clark-Lewis et al (1988) Proc. Natl. Acad. Sci. U.S.A. 65: 7897–7902, may be used to determine the extent of folding. In addition, folding may be monitored on the analytical HPLC column by observing the appearance of a peak corresponding to the folded form that has a retention time approximately 3 min. earlier than the reduced form. In the examples below, at least 80% folding was observed except in respect of the 7–72 analog which, when acetylated at the NH-terminus, was found to fold quantitatively. All the purified folded analogs in the following examples failed to react with Ellman's reagent, indicating the absence of free cysteine.

Analog purity may be assessed on the analytical HPLC column or by other means such as isoelectric focusing. A protocol for isoelectric focusing is as follows. Mini polyacrylamide gels (Pharmacia "PHAST" gels, IEF 3–9; Pharmacia, Uppsala, Sweden) are washed in 8M urea and then in 8M urea containing pH 9–11 Ampholytes (Pharmacia), for 30 min each, either with or without 10 μg/ml dithiothreitol. Gels are prerun for 15 V-h at 200-V, 2.0-mA, 3.0-mW maximum settings, and the samples are loaded and run for 410 v-h at 1000-V, 5.0-mA, 3.0-mW maximum settings on the Pharmacia "PHAST" system for a total of 500-V with maximum settings of 2.0-mW, 5.0-mA, and 100-V. The pH gradient may be determined by using a surface pH electrode. The gels are stained with silver by using the "PHAST" developing system as described in the manual.

The structure of the analogs may be determined by protein sequencing, for example by using the following protocol. Protein sequences are determined by Edman degradations using either solid-phase or gas-liquid-phase methods. For solid-phase sequence analysis, reduced and carboxymethylated protein or proteolytic cleavage fragments are coupled to arylamine-functionalized poly (vinylidenedifluoride) membranes (Sequelon AA; Milligen/Biosearch, Burlington, Mass.) using the water-soluable carbodiimide 1-ethyl-3-[3-)dimethylamino)propul]carbodiimide hydrochloride and sequenced in a Milligen/Biosearch Model 6600 sequencer using standard protocols. For gas-liquid-phase sequence analysis, polypeptides are applied to Polybrene-coated glass fibre disks and sequenced in an Applied Biosystems Model 477 protein sequencer using standard protocols. Sequencing of protected peptide resins is carried out on $N^\alpha$-deprotected samples by using the same methods. N-Terminal solid-phase sequencing runs usually reveal a major portion of the sequence. The remaining sequence may be obtained by runs of HPLC-fractionated fragments, derived either by proteolytic cleavage with Asp-N-endoprotease (Boehringer Mannheim Canada, Laval, Quebec) or by chemical cleavage, through preferential hydrolysis of the Asp-Pro peptide bond in dilute formic acid.

For the biological assays referred to in the following examples, human neutrophils isolated from buffy coats of donor blood were placed in a final suspension of $10^8$ cells/ml kept at 0.15mM MaCl, 0.05 mM $CaCl_2$ at 10° C. until use. Competition binding studies were performed according to the following protocol. IL-8 was iodinated with Enzymobead reagent (Bio-Rad) as instructed by the supplier. Briefly, 1 nmol of IL-8 was mixed with 50 µl of rehydrated Enzymobead reagent, 50 µl of 0.2M potassium phosphate, pH 7.2, 2 mCl or $Na^{125}I$, and 25 ml of 2% D(+)-glucose and incubated for 30 min at 21° C. After stopping the reaction with 50 µl of 1M KI, the protein is separated from label by desalting on Bio-Gel P6DG. The $^{125}I$-IL-8 preparations were each analyzed for purity (SDS-polyacrylamide gel electrophoresis) and binding capacity (self-displacement analysis using freshly isolated human neutrophils) prior to use. Neutrophils ($2\times10^8$) in 120 µl of RPMI 1640 medium containing 20 mM Hepes, pH 7.3, and 10 mg/ml BSA (binding medium) are incubated on ice (0°–4° C.) for 90 min with 1 nM $^{125}I$-IL-8 in the presence or absence of cold competitor ($10^{-11}$ to $10^{-5}$). Cells are separated from unbound radioactivity by centrifugation for 1 min at 8000× g through 350 µl of phosphate-buffered saline (PBS) containing 60 mg/ml BSA (wash medium) in a Hettich Microliter centrifuge model 2020. The supernatant is aspirated, and the bottom of the tubes containing the cell sediment is sliced off and counted in a MR 480 automated µ counter (kontron). The $K_d$ values were determined by calculating nonlinear least squares fits of the measured data, based on a single binding site model, and determining the $K_d$ using a LIGAND program as described by Moser, et al (1991) J. Biol. Chem. 266: 10666–10671.

EXAMPLE 1

Analogs of monomers of IL-8 as described in Table 1 were synthesized according to the preceding methods and folded to produce analog cytokines. In addition, IL-8 1–72 and the 77-residue form of IL-8 were synthesized.

Cytokine analogs formed from the monomers described in Table 1 were compared for biological activity according to in vitro assays described herein. Table 1 shows the $ED_{50}$ values of the indicated analogs estimated from the data shown in FIGS. 1, 2, 3, and 4 by determining the protein concentration (nanomolar) at 50% of the maximum response that was observed with IL-8 1–72. The binding dissociation constants ($K_d$ values) were calculated from the competitive binding data shown in FIGS. 5 and 6 as described above.

TABLE 1

| Analog | Elastase $ED_{50}$ | Chemotaxis $ED_{50}$ | Binding $K_d$ |
|---|---|---|---|
| 1-71 | 12.0 | 0.38 | 0.25 |
| 77-residue IL-8 | 25.0 | 0.69 | 0.35 |
| 3-72 | 2.5 | 0.21 | 0.18 |
| 4-72 | 4.5 | 0.25 | 0.22 |
| 5-72 | 1000.0 | 0.48 | 0.76 |
| 6-72 | Undetectable | Undetectable | 31.0 |
| 7-72 | Undetectable | Undetectable | Undetectable |
| 1-72 | 13.0 | 0.36 | 0.25 |
| 1-69 | 7.5 | 0.14 | 0.15 |
| 1-66 | 13.0 | 0.32 | 0.32 |
| 1-63 | 150.0 | 1.7 | 3.4 |
| 1-60 | 220.0 | 3.9 | 7.3 |
| 1-58 | 680.0 | 8.9 | 22.0 |
| 1-54 | 580.0 | 6.7 | 10.0 |
| 1-51 | 680.0 | 7.1 | 17.0 |

IL-8 1–72; 77-residue IL-8; 3–72; and, 4–72 analogs demonstrated concentration dependent responses in neutrophil and elastase release and chemotaxis assays. Compared to IL-8 1–72, the 4–72 and 3–72 analogs had respectively, an approximate 3 and 5 fold higher potency in the elastase release assay. The 7-residue IL-8 was approximately 2 fold less potent than IL-8. The 3–72 and 4–72 analogs were both about 2 fold more potent than IL-8 1–72 in the chemotaxis assay. The binding studies show that the 3–72 and 4–72 analogs displaced labelled IL-8 with efficiencies close to that of IL-8 but the 77-residue form required significantly higher concentrations.

The 7–72 and 6–72 analogs were inactive in both the elastase release and the chemotaxis assays. The 5–72 analog exhibited an approximately 80 fold lower $ED_{50}$ in the elastase release assay as compared to IL-8 but the chemotaxis potency of the 5–72 analog was only slightly lower. The 5–72 and 6–72 analogs also competed well with IL-8 for neutrophil binding with the 5–72 form showing a stronger ability to compete.

The 1–66 analog had approximately equivalent potency and the 1–69 analog had about a 2 fold higher potency, than the 1–72 form in the elastase release assay. The potency of the 1–63 and 1–60 analogs were respectively, approximately 12 and 17 fold lower than the 1–72 form. Elastase release activity was readily detectable, but about 50 fold lower in potency with the 1–58, 1–54, and 1–51 analogs. The same pattern of relative potencies for the COOH-terminus analogs was observed in the chemotaxis assays.

All the COOH-terminus analogs were capable of competing with IL-8 1–72 for binding to human neutrophils. The 1–72, 1–69, and 1–66 forms were approximately equivalent in competing with the labelled ligand. The 1–63 and 1–60 forms showed an approximate 13 and 29 fold reduction, respectively. The 1–5.8, 1–54, and 1–51 forms showed an approximately 40–80 fold less effective ability to compete for binding that IL-8 1–72. Thus, the 1–51 analog with the entire 21 amino acid COOH-terminal region deleted had detectable activity and was able to compete fully for IL-8 binding, although its effectiveness was reduced.

EXAMPLE 2

As shown in Example 1, a COOH-terminally truncated 1–51 analog showed reduced activity in all three assays as compared to IL-8 1–72. The elastase release activity assay was repeated using increasing concentrations of a peptide synthesized according to the preceding methods having the sequence of IL-8 residues 51–72. The IL-8 51–72 peptide was employed in increasing concentrations together with the cytokine analog IL-8 1–51 at $10^{-7}$M. FIG. 7 shows that the 51–72 peptide at high concentrations ($10^{-4}$M) provided an approximated 2 fold increase in the activity of IL-8 1–51. The 51–72 peptide alone at concentrations up to $10^{-4}$M did not stimulate elastase release, chemotaxis, or receptor binding.

EXAMPLE 3

Analog cytokines having residues 5–72; 6–72; and 7–72; respectively, were synthesized according to the method described herein. FIG. 8 shows the results of an assay for elastase release by human neutrophils pretreated with cytochalasin B and stimulated with $10^{-8}$M IL-8 1–72 in the presence of increasing concentrations of the analog cytokines IL-8 5–72 (▲); IL-8 6–72 (●), and IL-8 7–72 (■). The assay was performed as previously described and elastase release is expressed in relative fluorescence units (1 unit=1 pMol 7-amino-4-methylcoumarine produced min). Mean values were determined from duplicate determinations form one out of three similar experiments performed with different neutrophil preparations. Results show that, of the three analogs tested, the 6–72 form was most effective in blocking elastase release activity of IL-8 1–72.

As is shown in FIG. 9, samples of $2\times10^6$ neutrophils were incubated for 90 min at 0°–4° C with $10^{-9}$M $^{125}$I-IL-8 1–72 in the presence of increasing concentrations of unlabelled IL-8 1–72 (○), IL-8 5–72 (◇), IL-8 6–72 (△) and IL-8 7–72 (□), respectively, and the binding of $^{125}$I-IL-8 1–72 was determined. The results are means of duplicate measurements representative of three independent experiments performed according to the methods described herein. The results show a lack of competitive binding by the 7–72 analog. The 5–72 analog demonstrated competitive binding close to that of unlabelled IL-8 1–72. The 6–72 analog demonstrated competitive binding at a reduced level.

EXAMPLE 4

The ability of cytokine analog IL-8 6–72 to inhibit neutrophil activation was further investigated, As is shown in FIG. 10, release of elastase by cytochalasin B-treated human neutrophils stimulated with $10^{-8}$M IL-8 (● or $10^{-8}$M fMet-Leu-Phe (▲) in the presence of increasing concentrations of IL-8 6–72 was investigated. The effect of IL-8 6–72 alone was also tested (○). The results are mean values of duplicates from three experiments with different neutrophil preparations according to the methods described herein. The results show that IL-8 6–72 is ineffective in neutrophil activations and will compete with IL-8 1–72 to block neutrophil activation.

As is shown in FIG. 11, migrations of human neutrophils as the indicated concentrations of IL-8 6–72 in the presence (● and absence (○) of $10^{-8}$M IL-8 1–72 was investigated. The results are relative values with respect to non-inhibited controls and are mean values of duplicates form two independent experiments with different neutrophil preparations performed according to the procedures described herein. The results show that, in respect of neutrophil chemotaxis, IL-8 6–72 has a much decreased activity as compared to IL-8 1–72 and, the former will compete with the latter to inhibit chemotaxis.

The formation of $H_2O_2$ by human neutrophils after stimulation with $10^{-8}$M IL-8 1–72 in the presence of IL-8 6–72 at concentrations varying form 0–$10^{-6}$M was tested. Increasing concentrations of IL-8 6–72 resulted in a reduction of the amount to $H_2 O_2$ produced. IL-8 6–72 alone was ineffective in stimulating the respiratory burst.

EXAMPLE 5

As is shown in FIG. 12, IL-8 6–72 inhibits neutrophil activation by IL-8 1–72 (●, GROα (■) and NAP-2 (▲). The figure shows elastase release by cytochalasin B-treated human neutrophils stimulated with IL-8 1–72 and the homologues at $10^{-8}$M in the presence of increasing concentrations of IL-8 6–72. The results are mean values of duplicate determinations from one out of two similar experiments with different neutrophil preparations, performed according to the procedures described herein. NAP-2 refers to neutrophil activating peptide-2 as described by Walz and Baggiolini (1989) Biochem. Biophys. Res. Commun. 159: 969–975. GROα refers to a substance having melanoma growth stimulating activity described in Richmond, et al (1988) Embo. J. 7: 2025–2033.

The behaviour of the 5–72 analog is that of a partial antagonist wherein receptor binding is relatively high but effectiveness in receptor signalling is reduced. Given its binding affinity, it can be expected that cytokine analog IL-8 5–72 will be an effective IL-8 mediating agent, particularly in circumstances where its chemotaxis activity is desirable.

EXAMPLE 6

The effect of amino acid replacement on the activity of interleukin-8 analogues was also explored, using compounds prepared by t-boc-based solid phase peptide synthesis. Results are presented in table 2 (Orn=ornithine).

TABLE 2

| Analogue/Variant | N-terminal sequence | | | | | | | | | Kd (nM) | IC$_{50}$ (μM) |
|---|---|---|---|---|---|---|---|---|---|---|---|
| | 1 | 2 | 3 | 4 | 5 | 6 | 7 | 8 | 9 | | |
| (SEQ ID NO: 1) IL-8 (1-72) | Ser- | Ala- | Lys- | Glu- | Leu- | Arg- | Cys- | Gln- | Cys... | 0.25 | |
| (SEQ ID NO: 2) IL-8 (4-72) | | | | Glu- | Leu- | Arg- | Cys- | Gln- | Cys... | 0.22 | |
| (SEQ ID NO: 3) IL-8, ELQ (7-72) | | | | Glu- | Leu- | Gln- | Cys- | Gln- | Cys... | 650 | 1.1 |
| (SEQ ID NO: 4) IL-8, ELL (7-72) | | | | Glu- | Leu- | Leu- | Cys- | Gln- | Cys... | 1290 | 0.7 |
| (SEQ ID NO: 5) IL-8, ELK (7-72) | | | | Glu- | Leu- | Lys- | Cys- | Gln- | Cys... | 220 | 1.8 |
| (SEQ ID NO: 6) IL-8, ELOrn (7-72) | | | | Glu- | Leu- | Orn- | Cys- | Gln- | Cys... | 400 | 5.4 |
| (SEQ ID NO: 7) IL-8, ELNle (7-72) | | | | Glu- | Leu- | Nle- | Cys- | Gln- | Cys... | 170 | 1.0 |
| (SEQ ID NO: 8) IL-8, AAR (7-72) | | | | Ala- | Ala- | Arg- | Cys- | Gln- | Cys... | 7.9 | 0.3 |
| (SEQ ID NO: 9) IL-8 (5-72) | | | | | Leu- | Arg- | Cys- | Gln- | Cys... | 0.8 | |
| (SEQ ID NO: 10) IL-8, IR (7-72) | | | | | Ile- | Arg- | Cys- | Gln- | Cys... | 16 | 0.3 |
| (SEQ ID NO: 11) IL-8, QR (7-72) | | | | | Gln- | Arg- | Cys- | Gln- | Cys... | 34 | 2.1 |
| (SEQ ID NO: 12) IL-8 (6-72) | | | | | | Arg- | Cys- | Gln- | Cys... | 50 | 0.3 |
| (SEQ ID NO: 13) IL-8 (7-72) | | | | | | | Cys- | Gln- | Cys...>10,000 | | |

From these results, it is evident that all analogues extended N-terminally from the core IL-8(7-72) region exhibit neutrophil binding affinity (Kd) that is at least in the μM range. Particularly useful as antagonists of interleukin-8 activity are those compounds having both a Kd value that is less than about 50 nM and an $IC_{50}$ value that is less than about 2.5 μM, such as IL-8, AAR (7-72); IL-8, IR (7-72); IL-8, QR (7-72) and IL-8 (6-72). Remarkably, these results also reveal a second class of IL-8 analogs capable of antagonizing the action of IL-8; those that despite having Kd values exceeding about 50 nM, nevertheless inhibit IL-8-mediated elastase release at concentrations not exceeding about 2.5 μM. Such potent IL-8 analogs include IL-8, ELL (7-72); IL-8, ELK (7-72); and IL-8, ELNle (7-72).

EXAMPLE 7

In vivo studies

The effect of various interleukin 8 analogs on inflammation was evaluated in vivo using the rabbit plasma exudation dermal assay reported previously by Beaubien et al, in Biochem. J., 1990, 271:801. In this model, inflammatory activity in the peritoneal exudate is monitored by its ability to induce oedema formation and neutrophil accumulation in rabbit skin. Briefly, rabbits were anaesthetized with sodium pentobarbitone, the dorsal skin was shaved and radiolabelled tracers ($^{125}$I-albumin and, in some experiments, $^{111}$In-neutrophils) were injected intravenously. Test samples suspended in phosphate buffered saline were injected intradermally (n=6). After four hours, the animals were killed with an anaesthetic overdose. The dorsal skin was removed, and the injection sites were punched out and counted for radioactivity in a multi-well Cobra Auto-Gamma radiation counter with spill-over correction (Packard).

Results (mean ±S.E.M.), presented in FIGS. 14 and 15, are expressed as μl of plasma/skin site (oedema formation) and $^{111}$In-neutrophil accumulation/skin site. It will be noted that both IL-8 (6-72) and the IL-8, AAR (5-72) analogs exhibited antagonism of IL-8 (1-72)-mediated oedema formation, and that neither analog exhibited a significant chemotactic effect on neutrophil accumulation.

Various changes and modifications may be made in practising this invention without departing from the spirit and scope thereof.

---

We claim:

1. An interleukin-8 (IL-8) analog comprising an amino acid sequence substantially equivalent to the human IL-8 1-72 sequence, wherein the amino acid sequence of said analog begins at residue Leu5 and continuing C-terminally at least to residue 51 or begins at residue Glu4, wherein said Glu4 is substituted for an amino acid other than Glu.

2. The interleukin-8 analog of claim 1, wherein the amino acid sequence thereof continues C-terminally at least to residue 66.

3. The interleukin-8 analog of claim 1, wherein the amino acid sequence thereof continues C-terminally at least to residue 69.

4. The interleukin-8 analog of claim 1, wherein the amino acid sequence thereof continues C-terminally at least to residue 72.

5. The interleukin-8 analog of claim 1, wherein at least one of residue Leu5 or Arg6 is replaced.

6. The interleukin-8 analog of claim 5, wherein Leu5 is replaced.

7. The interleukin-8 analog of claim 6, wherein residue Leu5 is replaced by an amino acid selected such that the analog retains a Kd value that is about 50 nM or less and $IC_{50}$ value, as determined in an elastase release assay, of less that about 2.5 uM.

8. The interleukin-8 analog of claim 6, wherein residue Leu5 is replaced by an amino acid selected from the group consisting of glutamine and isoleucine.

9. The interleukin-8 analog of claim 8, which is human IL-8, Ile5 (6-72) (SEQ ID NO:10).

10. The interleukin-8 analog of claim 8, which is human IL-8, Gln5 (6-72) (SEQ NO:11).

11. The interleukin-8 analog of claim 5, wherein said analog contains a N-terminal residue other than the naturally occurring Glu4.

12. The interleukin-8 analog of claim 11, wherein said analog is Ala4 Ala5 (6-72) (SEQ ID NO:8).

13. The interleukin-8 analog of claim 1, wherein residue Leu5 is deleted.

14. The interleukin-8 analog of claim 13, wherein residue Leu5 is deleted.

15. The interleukin-8 analog of claim 1, which is human IL-8)5-72) (SEQ ID NO:9).

16. The interleukin-8 analog of claim 1, wherein residue Arg6 is replaced.

17. The interleukin-8 analog of claim 16, wherein residue Arg6 is replaced by an amino acid selected to confer on said analog a Kd value greater than about 50 nM and an $IC_{50}$ value, as determined in an elastase release assay, of less than 2.5 µM.

18. The interleukin-8 analog of claim 16, wherein residue Arg6 is replaced by an amino acid selected from the group consisting of leucine, norleucine and lysine.

19. The interleukin-8 analog of claim 16, wherein said analog has an additional N-terminal residue and said analog is selected from the group consisting of human IL-8, Glu4 Leu5 Leu6 (7-72) (SEQ ID NO:4), human IL-8, Glu4 Leu5 Nle6 (7-72) (SEQ ID NO:7), and human IL-9, Glu4 Leu5 Lys6 (7-72) (SEQ ID NO:5).

20. The interleukin-8 analog of claim 16, wherein said analog has an additional N-terminal residue and said analog is human IL-8 Glu4 Leu5 Gln6 (7-72) (SEQ ID NO:3).

21. A pharmaceutical composition comprising the interleukin-8 analog of claim 1 and a carrier.

22. A biologically active analog of human interleukin-8 (IL-8), the analog having amino acid sequence substantially equivalent to the IL-8 sequence beginning at residue 3 and continuing C-terminally to a residue between residues 50 and 70.

23. A pharmaceutical composition comprising the biologically active human interleukin-8 analog of claim 22 and a carrier.

24. The biologically active human interleukin-8 analog of claim 22 wherein residue 3 is deleted.

25. A pharmaceutical composition comprising the biologically active human interleukin-8 analog of claim 24 and a carrier.

26. The biologically active human interleukin-8 analog of claim 22, the analog having a sequence that continues C-terminally at least to residue 66.

27. The biologically active human interleukin-8 analog of claim 26 wherein residue 3 is deleted.

28. The biologically active human interleukin-8 analog of claim 22, which is IL-8 (SEQ ID NO:14).

* * * * *

UNITED STATES PATENT AND TRADEMARK OFFICE
CERTIFICATE OF CORRECTION

PATENT NO. : 5,665,346　　　　　　　　　　　　　　　　　Page 1 of 2
DATED : September 9, 1997
INVENTOR(S) : Ian Clark-Lewis, et al.

It is certified that error appears in the above-identified patent and that said Letters Patent is hereby corrected as shown below:

Column 1, line 2, insert the following: --This invention was made with Government support under Grant No.1 RO1-GM-50969 awarded by the National Institutes of Health. The Government has certain rights in the invention.--

Column 1, line 36: "$K_4$" should read --$K_d$--

Column 3, lines 58 & 61: " ( ● " should read -- ( ● ) --

Column 4, lines 6, 9 & 16: " ( ● " should read -- ( ● ) --

Column 4, line 2: " ( ■ )" should read -- ( ● ) --

Column 4, line 28: "AAR7-12" should read --AAR7-72--

Column 4, line 61: "$Glu_4$" should read --$Glu^4$--

Column 6, line 30: "Geu" should read --Leu--

Column 6, line 48: "$Glu_4$" should read --$Glu^4$--

Column 7, line 31: "chanin" should read --chain--

Column 7, line 35: "Ash" should rad --Asn--

UNITED STATES PATENT AND TRADEMARK OFFICE
CERTIFICATE OF CORRECTION

PATENT NO. : 5,665,346
DATED : September 9, 1997
INVENTOR(S) : Ian Clark-Lewis, et al.

It is certified that error appears in the above-identified patent and that said Letters Patent is hereby corrected as shown below:

Column 7, line 52: "form" should read --from--

Column 10, line 54: "1-5.8" should read -- 1-58 --

Column 11, line 41: after "investigated" delete "," and insert -- . --

Column 12, lines 8 & 17: "form" should read --from--

Column 23, line 23, Claim 7: after "and" insert --an--

Column 23, line 25, Claim 7: "that" should read --than--

Column 23, line 25, Claim 7: "uM" should read -- µM --

Column 23, line 43, Claim 15: "IL-8)5-72)" should read --IL-8(5-72)--

Column 24, line 15, Claim 19: "IL-9" should read --IL-8--

Signed and Sealed this

Ninth Day of February, 1999

Attest:

*Attesting Officer*

*Acting Commissioner of Patents and Trademarks*